(12) United States Patent
Creemer et al.

(10) Patent No.: US 6,664,271 B1
(45) Date of Patent: Dec. 16, 2003

(54) IMMUNOPOTENTIATOR AGENTS

(75) Inventors: Lawrence Camillo Creemer, Greenfield, IN (US); Janice Rhea Herring, Indianapolis, IN (US); Edward Deorsey McGruder, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/980,961

(22) PCT Filed: May 11, 2000

(86) PCT No.: PCT/US00/06710
§ 371 (c)(1),
(2), (4) Date: Nov. 15, 2001

(87) PCT Pub. No.: WO00/71519
PCT Pub. Date: Nov. 30, 2000

Related U.S. Application Data

(60) Provisional application No. 60/135,338, filed on May 21, 1999.

(51) Int. Cl.$^7$ .................. A61K 31/445; C07D 409/06; C07D 211/60
(52) U.S. Cl. .................. 514/326; 514/304; 514/330; 546/124; 546/212; 546/225; 546/226; 546/227
(58) Field of Search .................. 514/304, 326, 514/330; 546/124, 212, 225, 226, 227

(56) References Cited

U.S. PATENT DOCUMENTS

| | | | |
|---|---|---|---|
| 4,402,961 A | | 9/1983 | Dubroeucq et al. |
| 4,528,294 A | | 7/1985 | Majoie et al. |
| 5,242,783 A | * | 9/1993 | Buchanan et al. .......... 430/446 |
| 5,407,943 A | * | 4/1995 | Yang .......................... 514/300 |
| 5,561,146 A | | 10/1996 | Kim et al. |
| 5,741,800 A | | 4/1998 | Webber et al. |

FOREIGN PATENT DOCUMENTS

| | | | |
|---|---|---|---|
| EP | 0623595 | | 11/1994 |
| WO | WO-98/46569 | | 4/1998 |
| WO | WO 02/068391 | * | 9/2002 |

OTHER PUBLICATIONS

Carelli et al. "Synthesis of 3-pyrroline and . . . " CA 62:66399 (1964), see RN 4451-86-9.*

Bettoni et al. "Absolute configuration and . . ." CA 77:61191 (1972), see RN 37736-43-9.*

Newman "Preparation of 6-acyl-3-biphenylmethyl . . . " CA 120:270443 (1994) see RN 154548-45-5.*

Conroy et al. "Using the electrostatic field effect . . . " CA 126:340334 (1997) see RN 159299-93-1.*

Yang et al. Potent 3-spiropiperidine growth hormone secretagogues CA 128:188304 (1998), see RN 116140-20-6.*

* cited by examiner

Primary Examiner—Ceila Chang
(74) Attorney, Agent, or Firm—John C. Demeter

(57) ABSTRACT

Novel compounds and methods for preparing same, immunopotentiating compositions, and a method for potentiating the immune system of a host animal. The method comprises administering to the animal an effective amount of an immunopotentiating compound of Formula I or Formula II, or a physiologically acceptable salt.

17 Claims, No Drawings

IMMUNOPOTENTIATOR AGENTS

This application is a 371 of PCT/US00/06710 filed May 11, 2000 which claimed priority benefit of Provisional Application Ser. No. 60/135,338 filed May 21, 1999.

BACKGROUND OF THE INVENTION

The present invention relates generally to agents useful for stimulating the immune system of a host animal, and more particularly, to agents and methods for providing selective stimulation to the immune system of a host animal.

A primary function of the immune system is to protect the animal against the deleterious effects of invading pathogens. One type of immune system response to such invasion, known as cell-mediated immune response, protects the animal against invasion by microorganisms, such as bacteria, protozoa and viruses, and also against invasion by abnormal and malignant cells. Cell-mediated immune response is controlled by the T-lymphocytes, or T-cells. When the body recognizes the presence of an invading pathogen, two types of T-cells are produced, namely cytotoxic, or killer, T-cells that can destroy the invading pathogen, and helper T-cells that enhance the body's defenses against the invader.

The immune system of an animal may become compromised due to such factors as disease, exposure to etiologic agents, allergic reactions, autoimmune system disorders and advanced age. When the animal becomes immunocompromised in this manner, the ability of the T-cells to destroy invading pathogens is reduced, and in severe cases, may be lost altogether. In addition, even when an animal has a functional immune system, the ability of the T-cells to resist infection by certain pathogens may be insufficient.

When the invading pathogen is a microorganism, such as a bacterium, it is common to administer antibiotics to the animal suffering from such invasion. The purpose of the antibiotics is to control the spread of the bacteria within the body, and preferably, to destroy it altogether. Many effective antibiotics have been developed to treat both humans and non-human animals against diseases caused by invading etiologic agents. The effectiveness of these antibiotics has contributed to their widespread usage. However, this widespread usage of antibiotics has caused increased concern in recent years that antibiotic-resistant strains of bacteria may develop and spread. As a consequence, regulatory authorities have begun to more closely scrutinize and monitor the use of certain antimicrobial agents. In some cases, certain uses of these agents have been banned. In order to minimize the possibility that resistant bacterial strains may develop, it would be desirable to reduce the use of these antimicrobial agents. However, any such reduction would necessitate the development of new treatments to counter the harmful effects on the body that may be caused by an etiologic agent if left untreated.

It is believed that the class of drugs known as immunopotentiators acts on the immune system by priming the function of leukocytes, thereby enabling the leukocytes to respond with increased bactericidal activity upon stimulation by a pathogen. The inventors postulate that the mechanism of action of the immunopotentiators in the present application is a blastogenic effect on the T-cells, which is mediated by cytokines. The cytokines then prime the function of bactericidal leukocytes, such as macrophages, killer T-cells and polymorphonuclear leukocytes (PMNs). In the presence of pathogenic bacteria, the leukocytes phagocytize and kill the bacteria.

It is well known that certain bacterial agents are the source of numerous diseases afflicting animals. An example of an agent affecting both human and non-human animals is the bacterium *Escherichia coli*. Outbreaks caused by various strains of *E. coli* have been widely documented. Such outbreaks in humans are known to result from, among others, the consumption of undercooked and/or unwashed food. These outbreaks have been known to cause severe intestinal distress and, in some instances, death. The exposure to *E. coli* is also known to cause severe problems in many animal species. For example, the syndrome avian colibacillosis is caused in poultry by *E. coli*. Manifestations of colibacillosis in poultry may include acute septicemia, airsacculitis, pericarditis, perihepatitis and peritonitis. The control of this disease is economically important to poultry producers, because it causes morbidity, mortality, lack of uniformity, decreased performance and increased condemnations.

Etiologic agents such as *E. coli* are often secondary pathogens to a primary viral insult. However, some virulent bacterial isolates are known to cause disease even in the absence of a primary insult. *E. coli* causes airsacculitis in poultry by colonizing in the air sac following a reduction in respiratory host defenses, which is often a sequelae to stressors or viral infections, such as infectious bronchitis virus and Newcastle's disease virus. Presently, colibacillosis in poultry is prevented by the early administration of antimicrobial agents such as cephalosporin, quinolone, and aminoglycoside antibiotic to one-day old chicks. However, in view of the concern that use of these antimicrobial agents may contribute to the development of antibiotic-resistant bacteria, it is desirable to reduce such use.

In addition, due to the crowded pens and unsanitary structures that are often used to house non-human animals, these animals are at a high risk of infection and re-infection, and of immune system disorders occurring as a result of such conditions. In many cases, an infected and/or immunocompromised animal must be treated with antibiotics in order to prevent and/or attempt to control the disease.

Accordingly, it is desired to provide a class of compounds that stimulates the natural immune system of a host animal, thereby enabling the host animal to increase its resistance to infection. In addition, it is desired to provide a class of compounds that provides an alternative to the use of antibiotics.

SUMMARY OF THE INVENTION

A class of drugs, known as immunopotentiators, is provided. These drugs, when introduced into the body of a host animal, selectively stimulate the natural immune system of the host, thereby reducing or eliminating altogether the necessity to introduce antibiotics into the host's body in order to fight certain infectious agents. As a result of this selective stimulation, i.e., T-cell blastogenesis and production of cytokines, the natural immune system of the host animal achieves an enhanced ability to control the bacteria.

In one aspect of the present invention, there is provided an immunopotentiating composition comprising a physiologically acceptable carrier and an effective immunopotentiating amount of a compound defined by the following Formula I:

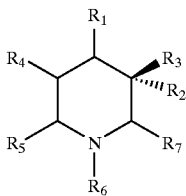

wherein:

$R_1$ is H, $C_1$–$C_4$ alkyl or (=O);

$R_2$ is $C(O)R_8$, $CH_2C(O)R_8$, CN, $CH_2OH$, OH, $OC(O)R_9$ or $OS(O)_2R_9$;

$R_3$, $R_4$ and $R_5$ are each independently H or $C_1$–$C_4$ alkyl;

$R_6$ is $C(O)OCH_2Ar_3$, $C(O)NHCH_2Ar_3$, $C(O)Ar_1$, $C(O)CH(R_3)Ar_2$, $C(O)CH(R_3)CH_2Ar_2$, $C(O)CH(R_3)CH_2CH_2Ar_4$ or $C(O)NHR_9$;

$R_7$ is H or $CH_2C(O)R_8$;

$R_8$ is H, $C_1$–$C_4$ alkyl, $OR_{10}$, $NHR_{11}$ or OH (when $R_6$ is $C(O)Ar$, or $C(O)CH(R_3)Ar_2$);

$R_9$ is $C_1$–$C_4$ alkyl;

$R_{10}$ is $C_2$–$C_8$ alkyl, $CH_2CH_2N(CH_3)_2$ or $CH_3$ (when $R_6$ is $C(O)Ar_1$ and $Ar_1$ is phenyl);

$R_{11}$ is $C_2$–$C_6$ alkyl, $CH_2CH_2N(CH_3)_2$ or $C_7$–$C_9$ alkyl (when $R_6$ is $C(O)Ar_1$);

$Ar_1$ is phenyl, 4-fluorophenyl, 2-thienyl, 3-thienyl or 1,4-biphenyl;

$Ar_2$ is phenyl or 2-thienyl;

$Ar_3$ is phenyl;

$Ar_4$ is 2-thienyl;

$Ar_5$ is phenyl or 2-halo-phenyl;

halo is Cl, Br or F; and $Ar_6$ is plienyl or 4-fluorophenyl;

with the proviso that when $R_7$ is $CH_2C(O)R_8$, then $R_2$ and $R_3$ are H, $R_4$ and $R_5$ are H or $C_1$–$C_4$ alkyl; $R_6$ is $C(O)CH(R_3)Ar_4$; $R_8$ is H, $C_1$–$C_4$ alkyl, $OR_9$ or $NHR_{10}$; $R_9$ is $C_1$–$C_8$ alkyl and $R_{10}$ is $C_2$–$C_8$ alkyl; and with the further proviso that when $R_1$ is (=O), then $R_2$ is $C(O)R_8$ or $CH_2C(O)R_8$; $R_3$, $R_4$ and $R_5$ are H or $C_1$–$C_4$ alkyl; $R_6$ is $C(O)OCH_2Ar_3$, $C(O)Ar_6$ or $C(O)NHR_9$; $R_7$ is H or, together with $R_5$, $CH_2CH_2$; $R_8$ is H, $C_1$–$C_4$ alkyl, $OR_{10}$ or $NHR_{11}$; $R_9$ is $C_1$–$C_4$ alkyl; $R_{10}$ is $C_1$–$C_8$ alkyl and $R_{11}$ is $C_2$–$C_8$ alkyl; or Formula II:

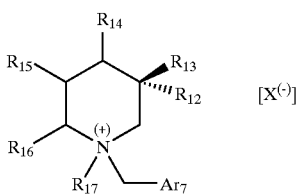

wherein:

$R_{12}$ is $C(O)R_{18}$ or $CH_2C(O)R_{18}$;

$R_{13}$, $R_{14}$, $R_{15}$ and $R_{16}$ are each independently H or $C_1$–$C_4$ alkyl;

$R_{17}$ is $C_1$–$C_4$ alkyl;

$R_{18}$ is H, $C_1$–$C_4$ alkyl; $OR_{19}$; $NHR_{20}$ or $N(CH_3)_2$;

$R_{19}$ is $C_1$–$C_8$ alkyl;

$R_{20}$ is $C_2$–$C_8$ alkyl;

$Ar_7$ is phenyl, 4-fluorophenyl or 1,3-thiazol-2-yl;

X is I, Cl, Br, $O(SO_2)R_{21}$; and $R_{21}$ is $CH_3$, $CF_3$, phenyl or p-methylphenyl;

or a physiologically acceptable salt of the compound of Formula I or Formula II.

In addition to the foregoing, another aspect of the invention is a method for potentiating the immune system of a host animal comprising administering to the host the immunopotentiating composition defined above. Yet another aspect of the invention is a method for protecting a host animal against infection, comprising administering to the host the immunopotentiating composition defined above.

A still further aspect of the invention is directed to certain novel compounds, and processes for preparing the novel compounds. The novel compounds are described by Formulas I and II as provided above, with the following additional provisos: when $R_1$, $R_4$, $R_5$ and $R_7$ are H, $R_2$ is $C(O)R_8$, $R_6$ is $C(O)Ar_3$ and $R_8$ is $OR_{10}$, then $R_3$ is not $C_1$ alkyl and $R_{10}$ is not $C_1$–$C_2$ alkyl; when $R_1$ is (=O), $R_2$ is $C(O)R_8$, $R_4$, $R_5$ and $R_7$ are H, $R_6$ is $C(O)Ar_6$, $R_8$ is $OR_{10}$ and $Ar_6$ is phenyl, then $R_3$ is not $C_2$ alkyl or $C_4$ alkyl and $R_{10}$ is not $C_1$–$C_2$ alkyl; when $R_1$ is (=O), $R_2$ is $C(O)R_8$, $R_3$, $R_4$, $R_5$ and $R_7$ are H, $R_6$ is $C(O)OCH_2Ar_6$, $R_8$ is $OR_{10}$ and $Ar_6$ is phenyl, then $R_{10}$ is not $C_1$–$C_2$ alkyl; when $R_1$, $R_3$, $R_4$, $R_5$ and $R_7$ are H, $R_2$ is $C(O)R_8$, $R_6$ is $C(O)CH_2Ar_3$ and $R_8$ is $OR_{10}$, then $R_{10}$ is not $C_2$ alkyl; and when $R_1$, $R_2$, $R_3$, $R_4$ and $R_5$ are H, $R_6$ is $C(O)Ar_5$, $R_7$ is $CH_2C(O)R_8$ and $Ar_5$ is phenyl, then $R_8$ is not $C_1$ alkyl or $NHR_{10}$ (when $R_{10}$ is $C_1$ alkyl).

DETAILED DESCRIPTION OF THE PREFERRED EMBODIMENTS

The present invention is directed to the use of certain compounds, known as immunopotentiators, to stimulate, or potentiate, the immune system of a host animal. More particularly, the invention relates to immunopotentiating compositions, and to a method for potentiating the immune system of a host animal having an immune system in need of potentiating, by administering to the host animal an effective amount of one or more immunopotentiating compounds represented generally by Formula I or Formula II, as defined and limited above, or a physiologically acceptable salt thereof.

The invention is also directed to a method for protecting a host animal against infection, and to certain novel compounds, as further defined and limited above.

As used herein, the chemical terms have their usual meanings unless otherwise indicated. For example, the term "alkyl" by itself or as part of another substituent, unless otherwise indicated, includes straight or branched aliphatic hydrocarbon radicals, such as, for example, methyl, ethyl, propyl, isopropyl, n-butyl, sec-butyl, isobutyl and tert-butyl, pentyl, hexyl, heptyl, octyl and nonyl groups having the indicated number of carbon atoms.

The term "Ar" refers to an aromatic or heteroaromatic group, or a substituted aromatic or heteroaromatic group.

The terms "immunopotentiator", "immunopotentiating agent" and "immunopotentiating compound" refer to an agent or compound capable of stimulating, enhancing or potentiating normal immune function, or restoring, stimulating, enhancing or potentiating a depressed immune function, or both.

The term "animal" includes all living organisms, exclusive of plants, insects and bacteria, having a responsive immune system and having T-cells capable of undergoing blastogenesis. The term is most particularly intended to include, but not be limited to, farm animals, such as all avian, bovine, ovine and porcine species; other mammals such as humans, non-human primates, canines and felines; and reptiles and fish.

The terms "effective amount" and "effective immunopotentiating amount" of a compound refer to the amount of that compound that will restore immune function to near normal levels, or increase immune function above normal levels in order to control or reduce infection.

A "physiologically acceptable salt" is a salt of a compound of the above-referenced Formula I or Formula II that is substantially non-toxic to a host animal.

The immunopotentiator compounds of the present invention have been found to enhance the blastogenesis of peripheral blood T-lymphocytes derived from avian, bovine, porcine, canine and non-human primates in vitro. Some of the immunopotentiator compounds used in the present invention have been found to be active in vitro at concentrations as low as 1 ng/ml. In many cases, the compounds are non-cytotoxic in vitro at concentrations up to 100 µg/ml, and in some cases, up to 1 mg/ml. Many compounds have been found to provide a rapid blastogenic response in vitro within 72 hours, and some have provided this response within 48 hours.

The present invention is further directed to certain novel compounds defined above, and subject to the specified limitations. The novel compounds, in most instances, are useful as immunopotentiating agents. Some of the novel compounds are useful as synthetic intermediates in the preparation of other immunopotentiating agents. In some cases, the immunopotentiator agents described for use in the inventive method are known compounds.

Although the invention is not so restricted, many of the compounds of Formula I of the present invention may be prepared by one of the synthetic routes described below, each of which involves the acylation of a starting amine. The starting amines utilized in these processes are either commercially available, or may be readily prepared by hydrogenation and, if necessary, subsequent oxidation of a corresponding pyridine. Generally speaking, the compounds of Formula I may be prepared by acylating an amine compound of Formula III

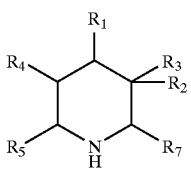

III with a compound of Formula IV $R_6Y$            IV wherein $R_1$, $R_2$, $R_3$, $R_4$, $R_5$, $R_6$ and $R_7$ are as previously defined; and Y is Cl, Br, or OH.

One synthetic route involves the dissolution of the appropriately substituted starting amine in dichloromethane. 1.1 molar equivalents of commercially available diisopropylethylamine (2.1 molar equivalents when the starting amine is in the salt form) is added to the mixture. Excessive temperature rise is controlled with an ambient temperature water bath (or ice water bath on larger scale reaction). 1.0 molar equivalents of the appropriately substituted acid chloride is then added slowly to control any rise in reaction temperature. After the addition of the acid chloride is completed, the mixture is allowed to stir at ambient temperature for approximately 1–4 hours. The mixture is then diluted with fresh dichloromethane, and washed with either 1 N HCl or water. The dichloromethane solution is then dried with anhydrous potassium carbonate and evaporated at ambient temperature under reduced pressure. The crude material is purified by high-vacuum short-path distillation, chromatography over silica gel, or reversed phase HPLC.

Another synthetic route involves suspending the appropriately substituted carboxylic acid in dichloromethane, and thereafter adding 1.0 molar equivalent of commercially available 1-(3-dimethylaniinopropyl)-3-ethylcarbodiimide hydrochloride, or alternatively, 1,3-dicyclohexylcarbodiimide (DCC). The mixture is allowed to stir at ambient temperature for approximately 1 hour. 1.0 molar equivalent of the appropriately substituted amine or alcohol is then added, and the mixture is stirred at ambient temperature for approximately 18 hours. The reaction mixture is diluted with fresh dichloromethane and then washed with water. The dichloromethane is dried with anhydrous potassium carbonate and evaporated at ambient temperature under reduced pressure. The crude material is then purified by either high-vacuum short-path distillation, chromatography over silica gel, or reversed phase HPLC.

Yet another synthetic route may be used when a urea is to be produced. In this case, the appropriately substituted starting amine is dissolved in dichloromethane, and 1.0 molar equivalent of the desired isocyanate is added. The mixture is then stirred at ambient temperature for approximately 3 hours. The mixture is diluted with fresh dichloromethane, and washed with water. The dichloromethane is dried with anhydrous potassium carbonate and evaporated at ambient temperature under reduced pressure. The crude material is then purified by either high-vacuum short-path distillation, chromatography over silica gel, or reversed phase HPLC.

The products obtained by the respective synthetic routes may then be further manipulated by means such as hydrolysis, alkylation, further acylation, reduction or oxidation to provide the desired analog. If desired, the compounds can be resolved by either utilizing chirally-resolved starting materials or by chiral resolution of the finished product.

Many of the compounds of Formula II may be prepared by either of the synthetic routes described below. Once again, the starting amines are either commercially available or may be prepared by the hydrogenation of a corresponding pyridine. Generally speaking, the compounds of Formula II may be prepared by alkylating an amine compound of Formula VII

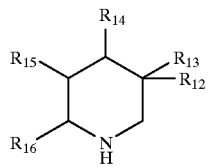

VII with a compound of Formula V $Ar_7CH_2X$            V or, reductively aminating the amine compound of Formula VII with a compound of Formula VI $Ar_7CHO$            VI and, quaternizing the resulting amine compound with a compound of Formula VIII $R_{17}X$           VIII wherein $R_{12}$, $R_{13}$, $R_{14}$, $R_{15}$ $R_{16}$, $R_{17}$, $Ar_7$ and X are as previously defined.

One synthetic route involves the alkylation and quaternization of the amine. In this process, the appropriately substituted starting amine is dissolved in dichloromethane. 1.1 molar equivalents of diisopropylethylamine is added followed by addition of an appropriately substituted bromide reagent. After the addition is complete the mixture is allowed to stir at ambient temperature for approximately 18–24 hours. The mixture is then evaporated at ambient temperature under reduced pressure and the crude product is purified by either high-vacuum short-path distillation, chromatography over silica gel, or reversed phase HPLC. This material is then dissolved in anhydrous diethyl ether and a large excess of methyl iodide is added. The mixture is then refluxed for 20–24 hours and resulting desired product precipitate is isolated by filtration.

Another synthetic route involves the reductive amination and quaternization of the amine. In this process, the appropriately substituted starting amine is dissolved in anhydrous methanol. 1.0 molar equivalents of commercially available aldehyde is added, followed by 1.9 molar equivalents of commercially available sodium cyanoborohydride. The mixture is then allowed to stir at ambient temperature for 20–24 hours. The mixture is diluted with dichloromethane and washed with water. The organic phase is separated, washed with saturated sodium chloride solution, dried with anhydrous potassium carbonate, and evaporated at ambient temperature under reduced pressure. The crude product is purified by either high-vacuum short-path distillation, chromatography over silica gel, or reversed phase HPLC. This material is then dissolved in anhydrous diethyl ether and a large excess of methyl iodide is added. This mixture is refluxed for 20–24 hours, and resulting desired product precipitate is isolated by filtration.

The products obtained by the synthetic routes for preparing the compounds of Formula II may be further manipulated by means such as hydrolysis, alkylation, further acylation, reduction or oxidation to provide the desired analog. Also, if desired, the compounds can be resolved by either utilizing chirally-resolved starting materials or by chiral resolution of the finished product.

Specific examples of the use of the synthetic schemes described above to prepare compounds of Formulas I and II are provided herein in preparative Examples 1–73. Preparative Examples 1–73 further illustrate processes for the preparation of many of the compounds of the present invention. It is not intended that the invention be limited in scope by reason of any of the examples. Certain compounds listed below can be used to prepare other compounds, as further described in the preparative examples.

Unless otherwise stated in the preparative examples, the starting materials and chemicals used to prepare the compounds of the present invention and the compounds employed in the present invention are either commercially available or are readily prepared by known processes.

The terms and abbreviations used in the examples have their normal meanings unless otherwise designated. For example, "° C." refers to degrees Celsius; "N" refers to normal or normality; "mmol" refers to millimole; "kg" refers to kilograms; "g" refers to grams; "mg" refers to milligrams; "μg" refers to micrograms; "ng" refers to nanograms; "ml" refers to milliliter; "M" refers to molar; and "MS" refers to mass spectrometry.

EXAMPLE 1

Preparation of Ethyl 1-Benzoyl-3-piperidinecarboxylate

Commercially available ethyl nipecotate (1.48 ml; 9.53 mmol) was dissolved in dichloromethane (20 ml), and diisopropylethylamine (1.82 ml; 10.45 mmol) was added. Benzoyl chloride (1.1 ml; 9.53 mmol) was then added slowly to control any rise in reaction temperature. After addition was complete the mixture was allowed to stir at ambient temperature for approximately 1–4 hours. The mixture was then diluted with fresh dichloromethane and washed with 1 N HCl. The dichloromethane solution was dried with anhydrous potassium carbonate and evaporated at ambient temperature under reduced pressure. The crude material was purified by high-vacuum distillation at approximately 200° C./0.1 torr giving ethyl 1-benzoyl-3-piperidinecarboxylate (2.38 g) as a colorless oil. (The temperatures given for distillations in these examples are oven temperatures and represent approximations. Similarly, the vacuum levels given for distillations are also approximates.) MS m/z (positive ion) 545 (dimer$^+$; 25), 284 (M+Na$^+$; 90), 262 (MH$^+$; 100), 216 (25).

EXAMPLE 2

Preparation of Ethyl 1-(3-thiophenecarbonyl)-3-piperidinecarboxylate

Commercially available 3-thiophene carboxylic acid (166.5 mg; 1.30 mmol) was suspended in dichloromethane (7 ml), and commercially available 1-(3-dimethylaminopropyl)-3-ethylcarbodiimide hydrochloride (252.8 mg; 1.32 mmol) was added. This mixture was allowed to stir at ambient temperature for 1 hour. Ethyl nipecotate (201 μl; 1.3 mmol) was then added, and stirring was continued for approximately 18 hours. The reaction mixture was then diluted with fresh dichloromethane and washed with water. The dichloromethane was dried with anhydrous potassium carbonate and evaporated at ambient temperature under reduced pressure. The crude material was purified by high-vacuum distillation at approximately 225° C./0.1 torr, and further by chromatography on silica, eluting with 50% ethyl acetate in hexane, giving ethyl 1-(3-thiophenecarbonyl)-3-piperidinecarboxylate (66.3 mg) as a colorless oil. MS m/z (positive ion) 268 (MH$^+$; 100).

EXAMPLE 3

Preparation of Ethyl 1-Benzoyl-4-oxo-3-piperidinecarboxylate

This compound was synthesized by the literature procedure described in *J. Chem. Soc.* (1967), p.2645. The crude product was purified by chromatography on silica eluting with 75–100% ethyl acetate in hexane as a step gradient. MS m/z (positive ion) 321 (M+2Na$^+$; 50), 298 (M$^+$Na$^+$; 45), 276 (MH$^+$; 100).

EXAMPLE 4

Preparation of Ethyl 1-Benzyloxycarbonyl-3-piperidinecarboxylate

The reaction was run in the same manner as ethyl 1-benzoyl-3-piperidinecarboxylate, starting with ethyl nipecotate (209.9 mg; 1.33 mmol and benzyl chloroformate (190 μl; 1.33 mmol). The crude product was distilled at 220° C./0.1 torr, giving ethyl 1-benzyloxycarbonyl-3- piperidinecarboxylate (236.5 mg) as a colorless oil. MS m/Z (positive ion) 539 ([dimer-OEt]$^+$; 50), 337 (M+2Na$^+$; 25), 314 (M+Na$^+$; 50), 292 (MH$^+$; 100), 247.5 (M-OEt; 90), 158 (50).

EXAMPLE 5

Preparation of 1-Benzoyl-3-piperidine Carboxylic Acid

Ethyl 1-benzoyl-3-piperidinecarboxylate (431.4 mg; 1.65 mmol) was dissolved in absolute ethanol (10 ml), and after addition of 1 N sodium hydroxide (20 ml), the mixture was allowed to stir at ambient temperature for approximately 1 hour. It was then poured into 1 N hydrochloric acid and extracted with dichloromethane. The dichloromethane was dried with anhydrous magnesium sulfate and then evaporated at ambient temperature under reduced pressure, giving 1-benzoyl-3-piperidine carboxylic acid (327.3 mg) as a white solid without further purification. MS m/z (negative ion) 232 (M-H; 100), 188 (M-CO$_2$H; 90).

EXAMPLE 6

Preparation of Ethyl 1-Phenylacetyl-3-piperidinecarboxylate

The reaction was run in the same manner as ethyl 1-benzoyl-3-piperidinecarboxylate, starting with ethyl nipecotate (215.8 mg; 1.37 mmol) and commercially available phenylacetyl chloride (180 µl; 1.37 mmol). The crude product was distilled at 220° C./0.1 torr, giving ethyl 1-phenylacetyl-3-piperidinecarboxylate (245.7 mg) as a pale yellow oil. MS m/z (positive ion) 298 (M+Na$^+$; 90), 276.5 (MH$^+$; 100), 230 (40), 158 (60).

EXAMPLE 7

Preparation of Ethyl 1-(4-Fluorobenzoyl)-3-piperidinecarboxylate

The reaction was run in the same manner as ethyl 1-benzoyl-3-piperidinecarboxylate, starting with ethyl nipecotate (230.9 mg; 1.47 mmol) and commercially available 4-fluorobenzoyl chloride (173 µl; 1.47 mmol). The crude product was distilled at 220° C./0.1 torr, giving ethyl 1-(4-fluorobenzoyl)-3-piperidinecarboxylate (283.4 mg) as a light yellow oil. MS m/z (positive ion) 581 (dimer+Na$^+$; 50), 302 (M+Na$^+$; 100), 280 (MH$^+$; 95), 234 (45), 229 (25), 158 (50), 122.5 (60).

EXAMPLE 8

Preparation of Ethyl (2-Thiophenecarbonyl)-3-piperidinecarboxylate

The reaction was run in the same manner as ethyl 1-benzoyl-3-piperidinecarboxylate, starting with ethyl nipecotate (202.9 mg; 1.29 mmol) and commercially available 2-thiophenecarbonyl chloride (138 µl; 1.29 mmol). The crude product was distilled at 225° C./0.1 torr, giving ethyl (2-thiophenecarbonyl)-3-piperidinecarboxylate (249.8 mg) as a yellow oil. MS m/z (positive ion) 290 (M+Na$^+$; 40), 268 (MH$^+$; 100).

EXAMPLE 9

Preparation of Ethyl 1-(2-thiopheneacetyl)-3-piperidinecarboxylate

The reaction was run in the same manner as ethyl 1-benzoyl-3-piperidinecarboxylate, starting with ethyl nipecotate (201.8 mg; 1.28 mmol) and commercially available 2-thiopheneacetyl chloride (158 µl; 1.28 mmol). The crude product was distilled at 225° C./0.1 torr, giving ethyl 1-(2-thiopheneacetyl)-3-piperidinecarboxylate (250.5 mg) as a yellow oil, which solidified on standing. MS m/z (positive ion) 304 (M+Na$^+$; 60), 282 (MH$^+$; 100).

EXAMPLE 10

Preparation of Ethyl 1-Benzyloxycarbonyl-4-oxo-3-piperidinecarboxylate

The reaction was run in the same manner as ethyl 1-benzoyl-3-piperidinecarboxylate, starting with commercially available ethyl 4-piperidone-3-carboxylate hydrochloride (203.2 mg; 0.98 mmol), diisopropylethylamine (360 µl; 2.08 mmol), and benzyl chloroformate (141 µl; 0.99 mmol). The crude product was purified by chromatography on silica eluting with 15% ethyl acetate in hexane, giving ethyl 1-benzyloxycarbonyl-4-oxo-3-piperidinecarboxylate (185.5 mg) as a colorless oil. MS m/z (positive ion) 323 (M+NH$_4^+$; 75), 306 (MH$^+$; 100), 262 (50).

EXAMPLE 11

Preparation of Ethyl 1-(N-Methylaminocarbonyl)-4-oxo-3-piperidinecarboxylate Commercially available ethyl 4-piperidone-3-carboxylate hydrochloride (203.2 mg; 0.98 mmol) was suspended in dichloromethane (7 ml), diisopropylethylamine (180 µl; 0.99 mmol) was added, followed by commercially available methyl isocyanate and (57 µl; 0.98 mmol). This mixture was stirred at ambient temperature for approximately 3 hours, and then diluted with fresh dichloromethane and washed with water. The dichloromethane solution was dried with anhydrous potassium carbonate and evaporated at ambient temperature under reduced pressure, giving ethyl 1-(N-methylaminocarbonyl)-4-oxo-3-piperidinecarboxylate (74.4 mg) as a white solid. MS m/z (positive ion) 479 (dimer+Na+; 40), 457 (dimer+; 25), 251 (M+Na$^+$; 100), 229 (MH$^+$; 90), 205 (25), 130 (25).

EXAMPLE 12

Preparation of Ethyl 1-(4-Fluorobenzoyl)-4-oxo-3-piperidinecarboxylate

The reaction was run in the same manner as ethyl 1-benzoyl-3-piperidinecarboxylate, starting with ethyl 4-piperidone-3-carboxylate hydrochloride (200.4 mg; 0.97 mmol), diisopropylethylamine (360 µl; 2.08 mmol) and 4-fluorobenzoyl chloride (114 µl; 0.97 mmol), giving ethyl 1-(4-fluorobenzoyl)4-oxo-3-piperidinecarboxylate (240.2 mg) as a thick, light yellow oil without further purification. MS m/z (positive ion) 348 (25), 316 (M+Na$^+$; 75), 294 (MH$^+$; 100).

EXAMPLE 13

Preparation of n-Butyl 1-Benzoyl-3-piperidinecarboxylate

The reaction was run in the same manner as ethyl 1-(3-thiophenecarbonyl)-3-piperidinecarboxylate, starting with 1-benzoyl-3-piperidine carboxylic acid (500 mg; 2.1 mmol) and commercially available n-butanol (500 µl; 5.5 mmol). The crude product was distilled at 225° C./0.1 torr, giving n-butyl 1-benzoyl-3-piperidinecarboxylate (258.2 mg) as a light yellow oil. MS m/z (positive ion) 312 (M+Na$^+$; 75), 290 (NH$^+$; 100).

EXAMPLE 14

Preparation of 1-Benzoyl-3-piperidinecarbonyl Chloride 1-benzoyl-3-piperidine carboxylic acid (1.01 g; 4.33 mmol) was suspended in dry dichloromethane (30 ml) under a nitrogen atmosphere. Thionyl chloride (3 ml; 41.3 mmol) was added and this mixture was heated to reflux for approximately 1 hour. It was then cooled to ambient temperature and evaporated under reduced pressure, giving 1-benzoyl-3-piperidinecarbonyl chloride (1.09 g) as a yellow oil. MS m/z (positive ion; run in $CH_3CN$) 503 (dimer$^+$; 30), 254 ([M+2]H$^+$; 35), 252 (MH$^+$; 100), 248 (50), 234 (60), 216 (25), 102 (30).

EXAMPLE 15

Preparation of (S)-Ethyl 1-Benzoyl-3-piperidinecarboxylate

The reaction was run in the same manner as ethyl 1-benzoyl-3-piperidinecarboxylate, starting with commercially available (S)-ethyl nipecotate (203 mg; 1.29 mmol; Chemi SpA; Italy) and benzoyl chloride (150 µl; 1.29 mmol). The crude product was distilled at 200° C./0.1 torr, giving (S)-ethyl 1-benzoyl-3-piperidinecarboxylate (171.7 mg) as a colorless oil. MS m/z (positive ion) 545 (dimer+Na$^+$; 15), 523 (dimer$^+$; 10), 284 (M+Na$^+$; 25), 262 (MH$^+$; 100).

EXAMPLE 16

Preparation of 1-(2-Thiopheneacetyl)-3-piperidine Carboxylic Acid

Ethyl 1-(2-thiopheneacetyl)-3-piperidinecarboxylate (256.4 mg; 0.91 mmol) was dissolved in absolute ethanol (5 ml). 1 N sodium hydroxide (10 ml) was added and the mixture was allowed to stir at ambient temperature for approximately 1 hour. It was then poured into 1 N HCl and extracted with dichloromethane. The dichloromethane was dried with magnesium sulfate and then evaporated at ambient temperature under reduced pressure, giving 1-(2-thiopheneacetyl)-3-piperidine carboxylic acid (210.1 mg) as a thick, yellow oil which solidified without further purification. MS m/z (positive ion) 254 (MH$^+$; 100).

EXAMPLE 17

Preparation of N-Ethyl 1-Benzoyl-3-piperidinecarboxamide

The reaction was run in the same manner as ethyl 1-benzoyl-3-piperidinecarboxylate, starting with 1-benzoyl-3-piperidinecarbonyl chloride (216.2 mg; 0.86 mmol), diisopropylethylamine (350 µl; 2.0 mmol) and commercially available ethylamine hydrochloride (74.6 mg; 0.86 mmol). The crude product was purified by chromatography on silica, eluting with 100% ethyl acetate, giving N-ethyl 1-benzoyl-3-piperidinecarboxamide (144.3 mg) as a white, sticky, semi-solid. MS m/z (positive ion) 362 (25), 261 (MH$^+$; 100).

EXAMPLE 18

Preparation of N-(n-Octyl) 1-Benzoyl-3-piperidinecarboxamide

The reaction was run in the same manner as ethyl 1-benzoyl-3-piperidinecarboxylate, starting with 1-benzoyl-3-piperidinecarbonyl chloride (219.0 mg; 0.87 mmol) and commercially available octylamine (144 µl; 0.87 mmol). The crude product was purified by chromatography on silica, eluting with 100% ethyl acetate, giving N-(n-octyl) 1-benzoyl-3-piperidinecarboxamide (207.5 mg) as a colorless waxy oil. MS m/z (positive ion) 345 (MH$^+$; 100), 216 (30).

EXAMPLE 19

Preparation of 1-(2-Thiopheneacetyl)-3-piperidinecarbonyl Chloride 1-(2-thiopheneacetyl)-3-piperidine carboxylic acid (1.3 g; 5.1 mmol) was dissolved in dry dichloromethane (35 ml) under a nitrogen atmosphere. Thionyl chloride (3 ml. 41.3 mmol) was added and the mixture was heated to reflux for approximately 1 hour. It was then cooled to ambient temperature and evaporated under reduced pressure, giving 1-(2-thiopheneacetyl)-3-piperidinecarbonyl chloride as a brownish oil. MS m/z (positive ion; run in $CH_3CN$) 274 ([M+2]H$^+$; 50), 272 (MH$^+$; 100).

EXAMPLE 20

Preparation of N-Ethyl 1-(2-Thiopheneacetyl)-3-piperidinecarboxamide

The reaction was run in the same manner as ethyl 1-benzoyl-3-piperidinecarboxylate, starting with 1-(2-thiopheneacetyl)-3-piperidinecarbonyl chloride (609.8 mg; 2.25 mmol), diisopropylethylamine (920 µl; 5.28 mmol) and commercially available ethylamine hydochloride (204.8 mg; 2.51 mmol). The crude product was purified by chromatography on silica, eluting with 100% ethyl acetate, giving N-ethyl 1-(2-thiopheneacetyl)-3-piperidinecarboxamide (437.5 mg) as a thick, brown syrup. MS m/z (positive ion) 303 (M+Na$^+$; 25), 281 (MH$^+$; 100), 157 (25).

EXAMPLE 21

Preparation of 3-(2-Thienyl)acrylic Acid

Commercially available 2-thiophene acrylonitrile (2.5 g; 18.5 mmol) was dissolved in 5 N sodium hydroxide (30 ml) with absolute methanol (30 ml) and heated to reflux for approximately 1 hr. The mixture was then allowed to cool to ambient temperature, acidified with 1 N HCl and extracted with dichloromethane. The dichloromethane was dried with magnesium sulfate and then evaporated at ambient temperature under reduced pressure, giving 3-(2-thienyl)acrylic acid (2.6 g) as a light yellow solid without further purification. MS m/z (negative ion) 307 (dimer; 25), 153 (M-H; 100).

EXAMPLE 22

Preparation of Ethyl 1-(3-(2-Thienyl)acrylyl)-3-piperidinecarboxylate

The reaction was run in the same manner as ethyl 1-(3-thiophenecarbonyl)-3-piperidinecarboxylate, starting with 3-(2-thienyl)acrylic acid (2.6 g; 16.9 mmol) and ethyl nipecotate (2.62 ml; 16.9 mmol). The crude product was purified by chromatography on silica, eluting with 40 to 100% ethyl acetate in hexane as a step gradient, giving ethyl 1-(3-(2-thienyl)acrylyl)-3-piperidinecarboxylate (1.74 g) as an off-white solid. MS m/z (positive ion) 316 (M+Na$^+$; 25), 294 (MH$^+$; 100).

EXAMPLE 23

Preparation of Ethyl 1-(3-(2-Thienyl)propionyl)3-piperidinecarboxylate

Ethyl 1-(3-(2-thienyl)acrylyl)-3-piperidinecarboxylate (404.1 mg; 1.38 mmol) was suspended in dimethyl sulfoxide (8 ml). The suspension was treated with hydrazine hydrate (1.7 ml; 54.7 mmol), saturated aqueous copper sulfate solution (6 drops), and glacial acetic acid (6 drops). This mixture was then stirred at ambient temperature and sodium periodate (1.47 g; 6.87 mmol) in water (20 ml) was added dropwise. After stirring an additional 1 hour, the mixture was taken up between aqueous 5% sodium thiosulfate and dichloromethane. The dichloromethane was separated, dried with anhydrous potassium carbonate, and evaporated at ambient temperature under reduced pressure. The crude product was purified by reverse phase chromatography on a $C_{18}$ column, eluting with 30:70 to 40:60 acetonitrile:water as a step gradient, giving ethyl 1-(3-(2-thienyl)propionyl)-3-piperidinecarboxylate (138 mg) as a colorless oil. MS m/z (positive ion) 296 (MH$^+$; 100).

EXAMPLE 24

Preparation of Ethyl 3-Piperidinylacetate

Commercially available ethyl-3-pyridylacetate (4.04 g; 24.5 mmol) was dissolved in absolute ethanol (100 ml). L(+) tartaric acid (3.67 g; 24.5 mmol) and platinum oxide (546.1 mg; 2.4 mmol) were added, and the partial suspension was placed under hydrogen gas at 50 psi with shaking for 24 hours. The hydrogen was removed, and the mixture was then filtered through celite to remove the catalyst. The filtrate was evaporated at ambient temperature under reduced pressure to a small volume. This residue was diluted with saturated sodium bicarbonate solution and extracted with ethyl acetate. The aqueous solution was then basified with 1 N sodium hydroxide and extracted with fresh ethyl acetate. The ethyl acetate extracts were combined, dried with anhydrous potassium carbonate, and evaporated at ambient temperature under reduced pressure, giving ethyl 3-piperidinylacetate (2.96 g) as a very pale yellow oil without further purification. MS m/z (positive ion) 172 (MH$^+$; 100).

EXAMPLE 25

Preparation of 2-Dimethylaminoethyl 1-(2-thiopheneacetyl)-3-piperidinecarboxamide The reaction was run in the same manner as ethyl 1-(3-thiophenecarbonyl)-3-piperidinecarboxylate, starting with 1-(2-thiopheneacetyl)-3-piperidine carboxylic acid (572.1 mg; 2.26 mmol) and commercially available N,N-dimethyl ethylenediamine (250 µl; 2.28 mmol). The crude product was purified by chromatography on silica, eluting with 70% methanol in dichloromethane, giving 2-dimethylaminoethyl 1-(2-thiopheneacetyl)-3-piperidinecarboxamide (128.3 mg) as a colorless oil. MS m/z (positive ion) 324 (MH$^+$; 100).

EXAMPLE 26

Preparation of Ethyl 2-Piperidinylacetate

The reaction was run in the same manner as ethyl 3-piperidinylacetate, starting with commercially available ethyl-2-pyridylacetate (4.00 g; 24.5 mmol). This gave ethyl 2-piperidinylacetate (2.41 g) as a light yellow oil without further purification. MS m/z (positive ion) 172 (MH$^+$; 100).

EXAMPLE 27

Preparation of Ethyl 1-(2-Thiopheneacetyl)-3-piperidinylacetate

The reaction was run in the same manner as ethyl 1-benzoyl-3-piperidinecarboxylate, starting with ethyl 3-piperidinylacetate (414.2 mg; 2.4 mmol) and 2-thiopheneacetyl chloride (295 µl; 2.4 mmol). The crude product was purified by chromatography on silica, eluting with 50% ethyl acetate in hexane, giving ethyl 1-(2-thiopheneacetyl)-3-piperidinylacetate (364 mg) as a pale yellow oil. MS m/z (positive ion) 318 (M+Na$^+$; 40), 296 (MH$^+$; 100).

EXAMPLE 28

Preparation of Ethyl 1-(2-Thiopheneacetyl)-2-piperidinylacetate

The reaction was run in the same manner as ethyl 1-benzoyl-3-piperidinecarboxylate, starting with ethyl 2-piperidinylacetate (405.1 mg; 2.37 mmol) and 2-thiopheneacetyl chloride (290 µl; 2.36 mmol). The crude product was purified by chromatography on silica, eluting with 50% ethyl acetate in hexane, giving ethyl 1-(2-thiopheneacetyl)-2-piperidinylacetate (439 mg) as a light yellow oil. MS m/z (positive ion) 296 (MH$^+$; 100).

EXAMPLE 29

Preparation of 1-Benzoyl-3-butyrylpiperidine 1-benzoyl-3-piperidinecarbonyl chloride (1.01 g; 4.02 mmol) was dissolved in dry tetrahydrofuran (30 ml) under a nitrogen atmosphere, and cooled to −20° C. Tributylphosphine (1.1 ml; 4.4 mmol) was then added and after 20 minutes of stirring at −20° C., propylmagnesium chloride (2 ml; 4.0 mmol; 2 M in ether) was added. After stirring for 5 minutes, the reaction was quenched by addition of 1 N HCl (5 ml), and the mixture was allowed to warm to ambient temperature. It was then diluted with 1 N HCl and extracted with diethyl ether. The ether was washed with saturated sodium bicarbonate solution, and then brine. It was then dried with anhydrous magnesium sulfate and evaporated at ambient temperature under reduced pressure. The crude product was purified by chromatography on silica eluting with 50% ethyl acetate in hexane, giving 1-benzoyl-3-butyrylpiperidine (401.7 mg) as a colorless oil. MS m/z (positive ion) 260 (MH$^+$; 100).

EXAMPLE 30

Preparation of (S)-Ethyl 1-(2-Thiopheneacetyl)-3-piperidinecarboxylate

The reaction was run in the same manner as ethyl 1-benzoyl-3-piperidinecarboxylate, starting with commercially available S-ethyl nipecotate (1.0 g; 6.37 mmol; Chemi SpA; Italy) and 2-thiopheneacetyl chloride (785 µl; 6.37 mmol). The crude product was distilled as 225° C./0.1 torr, giving (S)-ethyl 1-(2-thiopheneacetyl)-3-piperidinecarboxylate (1.23 g) as a light yellow oil. MS m/z (positive ion), 585 (dimer+Na$^+$; 10), 304 (M+Na$^+$; 50), 282 (MH$^+$; 100), 158 (50). OR (MeOH; 589) +62.96°. Product was shown to be >98% ee by chiral capillary electrophoresis using a 20% solution of --HSCD (highly sulfated cyclodextrin) at a voltage of 20 kV.

EXAMPLE 31

Preparation of Ethyl 6-Methyl-3-nicotinoate

Commercially available 6-methylnicotinic acid (4.96 g; 36.2 mmol) and molecular sieves (5 g) were suspended in absolute ethanol (200 ml). Concentrated $H_2SO_4$ (5 ml) was added and the mixture was heated to reflux for approximately 30 hours. It was then filtered, and evaporated to a small volume at ambient temperature under reduced pressure. The residue was diluted with 1 N sodium hydroxide and extracted with dichloromethane. The dichloromethane was separated, dried with anhydrous potassium carbonate, and evaporated at ambient temperature under reduced pressure, giving ethyl 6-methyl-3-nicotinoate (1.21 g) as a pale yellow oil without further purification. $^1$H-NMR (CDCl$_3$)·1.39 (t, 3H), 2.62 (s, 3H), 4.39 (q, 2H), 7.24 (d, 1H), 8.17 (d, 1H), 9.09 (s, 1H).

EXAMPLE 32

Preparation of Ethyl 6-Methyl-3-piperidinecarboxylate

The reaction was run in the same manner as ethyl 3-piperidinylacetate, starting with ethyl 6-methyl-3-nicotinoate (1.2 g; 7.27 mmol). This gave ethyl 6-methyl-3-piperidinecarboxylate (998.4 mg) as a colorless oil without further purification. MS m/z (positive ion) 172 (MH$^+$; 100), 102 (30).

EXAMPLE 33

Preparation of Ethyl 1-(2-Thiopheneacetyl)-6-methyl-3-piperidinecarboxylate

The reaction was run in the same manner as ethyl 1-benzoyl-3-piperidinecarboxylate, starting with ethyl 6-methyl-3-piperidinecarboxylate (263.1 mg; 1.54 mmol) and 2-thiopheneacetyl chloride (190 μl; 1.54 mmol). The crude product was distilled at 210° C./0.1 torr, giving ethyl 1-(2-thiopheneacetyl)-6-methyl-3-piperidinecarboxylate (272.2 mg) as a light yellow oil. MS m/z (positive ion) 591(dimer$^+$; 25) 296 (MH$^+$; 100).

EXAMPLE 34

Preparation of Ethyl 1-Benzyl-3-piperidinecarboxylate

Commercially available ethyl nipecotate (509.7 mg; 3.25 mmol) was dissolved in dichloromethane (12 ml). Diisopropylethylamine (570 μl; 3.27 mmol) was added, followed by commercially available benzyl bromide (386 μl; 3.25 mmol) and the mixture stirred at ambient temperature for approximately 20 hours. The mixture was then evaporated at ambient temperature under reduced pressure. The crude product was purified by chromatography on silica eluting with 80% ethyl acetate in hexane, giving ethyl 1-benzyl-3-piperidinecarboxylate (634.4 mg) as a colorless oil. MS m/z (positive ion) 248 (MH$^+$; 100).

EXAMPLE 35

Preparation of Ethyl 1-Benzyl-3-piperidinecarboxylate 1-Methiodide

Ethyl 1-benzyl-3-piperidinecarboxylate (590.6 mg; 2.39 mmol) was dissolved in diethyl ether (50 ml), and methyl iodide (2 ml) was added. This mixture was allowed to stir at ambient temperature for 3 days and was then heated to reflux for 23 hours. The precipitate was filtered, washed with fresh diethyl ether, and then dried under reduced pressure at ambient temperature, giving ethyl 1-benzyl-3-piperidinecarboxylate 1-methiodide (340.9 mg) as an off white solid. MS m/z (positive ion) 263 (MH$^+$; 30), 262 (M$^+$; 100).

EXAMPLE 36

Preparation of Ethyl 1-(4-Phenylbenzoyl)-3-piperidinecarboxylate

The reaction was run in the same manner as ethyl 1-benzoyl-3-piperidinecarboxylate, starting with ethyl nipecotate (504.4 mg; 3.2 mmol) and commercially available 4-biphenylcarbonyl chloride (693 mg; 3.21 mmol). The crude product was purified by chromatography on silica eluting with 30% ethyl acetate in hexane, giving ethyl 1-(4-phenylbenzoyl)-3-piperidinecarboxylate (805.5 mg) as a pale yellow oil. MS m/z (positive ion) 697 (dimer+Na$^+$; 15), 675 (dimer$^+$; 15), 360 (M+Na$^+$; 15), 338 (MH$^+$; 100), 181 (25).

EXAMPLE 37

Preparation of (S)-1-(2-Thiopheneacetyl)-3-piperidine Carboxylic Acid

This reaction was run in the same manner as 1-(2-thiopheneacetyl)-3-piperidine carboxylic acid, starting with (S)-ethyl 1-(2-thiopheneacetyl)-3-piperidinecarboxylate (10 g; 35.6). This gave (S)-1-(2-thiopheneacetyl)-3-piperidine carboxylic acid (9.27 g) as a white solid without further purification. MS m/z (positive ion) 506 (dimer$^+$; 25), 254 (MH$^+$; 100).

EXAMPLE 38

Preparation of Methyl 1-Benzyloxycarbonyl-4-oxo-3-piperidinecarboxylate

This compound may be prepared in the same manner as ethyl 1-benzoyl-3-piperidinecarboxylate, starting with commercially available methyl 4-oxo-3-piperidinecarboxylate hydrochloride, diisopropylethylaamine and commercially available benzyl chloroformate.

EXAMPLE 39

Preparation of Ethyl 1-Benzoyl-3-methyl-3-piperidinecarboxylate

This compound was synthesized by the literature procedure described in European Journal of Chemistry, Vol. 22, Page 383 (1987). The product was purified by chromatography on silica eluting with 30% ethyl acetate in hexane. MS m/z (positive ion) 573 (dimer+Na$^+$; 30), 276.5 (MH$^+$; 100).

EXAMPLE 40

Preparation of 8-[(Methylamino)carbonyl]-3-oxo-8-azabicyclo[3.2.1]octane-2-carboxylic Acid, Methyl Ester N-benzyltropinone (available from Crescent Chemical Co. Inc., Hauppage, N.Y.) is deprotonated with lithium diisopropylamide (LDA; generated from n-buLi and diisopropylamine) in THF under N$_2$ atmosphere at −78° C. CO$_2$ (gas or solid) is added, and the reaction is quenched by addition of iodomethane. The reaction mixture is then allowed to warm to ambient temperature, and after standard workup, is hydrogenated over Pd on carbon with trifluoroacetic acid in MeOH. The catalyst is filtered, and the solvent evaporated. Methylisocyanate and diisopropylethylamine in dichloromethane are then reacted with the hydrogenated product to provide, after standard workup, 8-[(methylamino) carbonyl]-3-oxo-8-azabicyclo[3.2.1]octane-2-carboxylic acid, methyl ester.

EXAMPLE 41

Preparation of 1-(2-Thiopheneacetyl)-3-hydroxypiperidine

This reaction was run in the same manner as ethyl 1-benzoyl-3-piperidinecarboxylate, starting with commercially available 3-hydroxypiperidine (1.03 g; 10.2 mmol) and 2-thiopheneacetyl chloride (1.2 ml; 10 mmol) and diisopropylethylamine (1.9 ml; 10.9 mmol). The crude product was purified by chromatography on silica, eluting with 100% ethyl acetate, giving 1-(2-thiopheneacetyl)-3-hydroxypiperidine (1.49 g) as a yellow oil, which solidified on standing. MS m/z (positive ion) 248 (M+Na$^+$; 50), 226 (MH$^+$; 100).

EXAMPLE 42

Preparation of (S)-1-(2-Thiopheneacetyl)-3-piperidinecarboxylic Acid Ammonium Salt A small amount of (S)-1-(2-thiopheneacetyl)-3-piperidine carboxylic acid was dissolved, with warming, in ethyl acetate. An excess amount of ammonia in methanol was added. Diethyl ether was then added to the cloudy mixture and a precipitate formed. The product was isolated by centrifugation and decanting, and was then dried under reduced pressure at ambient temperature. This gave (S)-1-(2-thiopheneacetyl)-3-piperidinecarboxylic acid ammonium salt as a white solid. MS m/z (positive ion) 254 (MH$^+$; 100).

EXAMPLE 43

Preparation of Ethyl 1-(1-Phenylpropionyl)-3-piperidinecarboxylate

This reaction was run in the same manner as ethyl 1-benzoyl-3-piperidinecarboxylate, starting with ethyl nipecotate (412.4 mg; 2.63 mmol), commercially available hydrocinnamoyl chloride (390 µl; 2.63 mmol), and diisopropylethylamine (550 µl; 3.16 mmol). The crude product was distilled at approximately 215° C./0.1 torr, giving ethyl 1-(1-phenylpropionyl)-3-piperidinecarboxylate (506.2 mg), as a colorless oil. MS m/z (positive ion) 290 (MH$^+$; 100).

EXAMPLE 44

Preparation of 1-(2-Thiopheneacetyl)-3-(O-methanesulfonyl)piperidine 1-(2-thiopheneacetyl)-3-hydroxypiperidine (1.2 g; 5.32 mmol) was dissolved is dichloromethane (20 ml), and diisopropylethylamine (1.1 ml; 6.3 mmol) was added. Methane sulfonyl chloride (410 µl; 5.32 mmol) was then added and mixture became warm to the touch. The mixture was allowed to stir at ambient temperature for 5 hours. The mixture was then diluted with dichloromethane and washed with water. The dichloromethane solution was dried with anhydrous magnesium sulfate and evaporated at ambient temperature under reduced pressure. The crude product was purified by chromatography on silica eluting with 70% ethyl acetate/30% hexane going to 100% ethyl acetate in a single step gradient, giving 1-(2-thiopheneacetyl)-3-(O-methanesulfonyl)piperidine (1.15 g) as a thick pale yellow oil. MS m/z (positive ion) 342 (M+K$^+$; 50), 326 (M+Na$^+$; 60), 304 (MH$^+$; 100).

EXAMPLE 45

Preparation of Ethyl 1-(2-Bromobenzoyl)-2-acetylpiperidinecarboxylate

This reaction was run in the same manner as ethyl 1-benzoyl-3-piperidinecarboxylate, starting with ethyl 2-piperidinylacetate (936.3 mg; 5.47 mmol), commercially available 2-bromobenzoylchloride (710 µl; 5.44 mmol), and diisopropylethylamine (1.1 ml; 6.3 mmol). The crude product was purified by chromatography on silica eluting with 50% ethyl acetate/50% hexane, giving ethyl 1-(2-bromobenzoyl)-2-acetylpiperidinecarboxylate (1.47 g) as a colorless oil. MS m/z (positive ion) 378 (M+Na$^+$+2; 40), 376 (M+Na$^+$; 35), 356 (MH$^+$+2; 100), 354 (MH$^+$; 95).

EXAMPLE 46

Preparation of 1-(2-Thiopheneacetyl)-3-(O-propionyl)piperidine 1-(2-thiopheneacetyl)-3-hydroxypiperidine (291 mg; 1.29 mmol) was dissolved in dichloromethane (8 ml), and diisopropylethylamine (250 µl; 1.4 mmol) was added. Commercially available propionyl chloride (115 µl; 1.32 mmol) was then added turning the mixture a light orange color. This mixture was allowed to stir at ambient temperature for 3 days. Additional propionyl chloride (150 µl; 1.73 mmol) was added and after 4 hours of additional stirring, additional diusopropylamine (200 µl; 1.15 mmol) was added. This mixture stirred at ambient temperature for 19 hours. It was then diluted with dichloromethane and washed with 1 N hydrochloric acid. The dichloromethane was dried with anhydrous magnesium sulfate and evaporated under reduced pressure at ambient temperature. The crude product was purified by chromatography on silica, eluting with 30% ethyl acetate/70% hexane to 100% ethyl acetate in a two step gradient, giving 1-(2-thiopheneacetyl)-3-(O-propionyl) piperidine (258.9 mg) as a colorless oil. MS m/z (positive ion) 585 (dimer+Na$^+$; 75), 563 (dimer$^+$; 50), 383 (60), 304 (M+Na$^+$; 85), 282 (MH$^+$; 100), 226 (40), 208 (60), 158 (65).

EXAMPLE 47

Preparation of (S)-di-(Ethylnipecotate)-L-(dibenzoyl)tartrate Salt

To a 3-neck, 5 liter flask equipped with a heating mantle, mechanical stirrer, temperature probe and reflux condenser topped with a calcium carbonate drying tube was charged 500.64 g (3.18 mol) of racemic ethyl nipecotate, followed by 2000 ml of 91% aqueous 2B-ethanol. To the solution was added 570.56 g (1.59 mol) of the resolving agent di-benzoyl-L-tartaric acid as a solid causing the temperature to rise to 47° C. Residual resolving agent was rinsed over with 502 ml of 91% ethanol. The mixture was heated to dissolve, and complete dissolution was observed at 79° C. The heat was turned off and the solution was allowed to gradually cool. The solution was seeded at 67° C. and allowed to cool slowly to room temperature and stirred a total of 15 hours after seeding. The white precipitate was collected and washed with 91% ethanol (2×350 ml) followed by vacuum drying at 45–50° C. for six hours to provide 366 g (34%) of the title compound as a white solid having a melting point of 173–175° C.>98% de. Analysis calculated for $C_{34}H_{44}N_2O_{12}$: C, 60.69; H, 6.59; N, 4.18. Found: C, 60.58; H, 6.66; N, 4.27.

EXAMPLE 48

Preparation of (S)-Ethyl 1-(N-Benzylurea)-3-piperidinecarboxylate (S)-di-(ethylnipecotate)-L-(dibenzoyl) tartrate salt (0.437 g; 0.65 mmol) was dissolved in dichloromethane (7 ml) and diisopropylethylamine (0.237 ml; 1.365 mmol) was added. Commercially available benzyl isocyanate (0.160 ml; 1.3 mmol) was then added. After the mixture was stirred for 2 hours at ambient temperature, more benzyl isocyanate (0.160 ml; 1.3 mmol) was added and the mixture was stirred an additional 12 hours. The mixture was then diluted with dichloromethane and washed with 1N HCl. The dichloromethane solution was dried with sodium chloride and evaporated at ambient temperature under reduced pressure. The crude material was purified by chromatography on silica, eluting with 20% ethyl acetate in hexane, giving (S)-ethyl 1-(N-benzylurea)-3-piperidinecarboxylate (200.0 mg) as a colorless oil. MS m/z (positive ion) 313 (M+Na$^+$; 55), 291 (MH$^+$; 100).

EXAMPLE 49

Preparation of (S)-Ethyl 1-(N-Methylurea)-3-piperidinecarboxylate (S)-di-(ethylnipecotate)-L-(dibenzoyl) tartrate salt (0.336 g; 0.5 mmol) was dissolved in dichloromethane (5 ml) and diisopropylethylamine (0.142 g; 1.1 mmol) was added. Commercially available methyl isocyanate (0.057 ml, 1.0 mmol) was then added. After the mixture was stirred for 2 hours at ambient temperature, more methyl isocyanate (0.057 ml; 1.0 mmol) was added and the mixture was stirred an additional 12 hours. The mixture was then diluted with dichloromethane and washed with 1N HCl. The dichloromethane solution was dried with sodium chloride and evaporated at ambient temperature under reduced pressure. The crude material was purified by chromatography on silica, eluting with 20% ethyl acetate in hexane, giving (S)-ethyl 1-(N-methylurea)-3-piperidinecarboxylate (136 mg) as a colorless oil. MS m/z (positive ion) 451 (dimer$^+$; 37), 237 (M+Na$^+$; 74), 215 (MH$^+$; 100).

EXAMPLE 50

Preparation of (S)-1-Benzoyl-3-piperidinecarboxylic Acid

The reaction was run in the same manner as 1-(2-thiopeneacetyl)-3-piperidine carboxylic acid, starting with (S)-ethyl 1-benzoyl-3-piperidinecarboxylate (8.71 g; 33.31 mmol), 1N sodium hydroxide (100 ml) and absolute ethanol (100 ml), giving (S)-1-benzoyl-3-piperidinecarboxylic acid as a white solid (7.20 g). MS m/z (negative ion) 232 ([M-H]$^-$; 100).

EXAMPLE 51

Preparation of (S)-1-Benzoyl-3-piperidinecarbonyl Chloride

The reaction was run in the same manner as 1-benzoyl-3-piperidinecarbonyl chloride, starting with (S)-1-benzoyl-3-piperidinecarboxylic acid (6.30 g; 27.0 mmols), thionyl chloride (16.06 g, 135 mmol), and dry dichloromethane (150 ml), giving (S)-1-benzoyl-3-piperidinecarbonyl chloride as a light yellow oil, which was used without further purification. MS (in CH3CN) m/z (positive ion) 503 (40), 485 (42), 467 (40), 254 (60), 252 (MH$^+$; 100), 234 (68).

EXAMPLE 52

Preparation of (S)-Methyl 1-Benzoyl-3-piperidinecarboxylate (S)-1-benzoyl-3-piperidinecarbonyl chloride (0.753 g; 3.0 mmol) was dissolved in dichloromethane (15 ml) and diisopropylethylamine (0.574 ml; 3.3 mmol) was added. Methanol (0.121 ml; 3.0 mmol) was then added and the mixture was stirred at ambient temperature for 4 hours. The mixture was then diluted with 1N HCl (25 ml) and fresh dichloromethane and separated. The dichloromethane was washed with water and dried with sodium chloride. The crude product was distilled at approximately 200° C./0.1 torr, giving (S)-methyl 1-benzoyl-3-piperidinecarboxylate (489.0 mg) as a clear oil. MS m/z (positive ion) 248 (MH$^+$; 85), 130 (100).

EXAMPLE 53

Preparation of (S)-Propyl 1-Benzoyl-3-piperidinecarboxylate

The reaction was run in the same manner as (S)-methyl 1-benzoyl-3-piperidinecarbbxylate, starting with (S)-1-benzoyl-3-piperidinecarbonyl chloride (0.7438 g, 2.9 mmol), diisopropylethylamine (0.4123 g; 3.19 mmol) and propanol (0.225 ml; 2.9 mmol). The crude product was distilled at approximately 225° C./0.1 torr, giving (S)-methyl 1-benzoyl-3-piperidinecarboxylate (550 mg) as a pale yellow oil. MS m/z (positive ion) 298 (M+Na$^+$; 45), 276 (MH$^+$; 100).

EXAMPLE 54

Preparation of (S)-Ethyl 1-(2-Thienylpropyl)-3-piperidinecarboxylate

This reaction was run in the same manner as ethyl 1-(3-thiophenecarbonyl)-3-piperidinecarboxylate, starting with commercially available 4-(2-thienyl)butyric acid (280 μl; 1.93 mmol), 1-(3-dimethylaminopropyl)-3-ethylcarbodiimide hydrochloride (367.7 mg; 1.92 mmol) and (S)-ethyl nipecotate (300 μl; 1.94 mmol). The crude product was purified by chromatography on silica eluting with 30% ethyl acetate l70% hexane to 40% ethyl acetate/ 60% hexane in a single step gradient, giving (S)-ethyl 1-(2-thienylpropyl)-3-piperidinecarboxylate (181.7 mg) as a colorless oil. MS m/z (positive ion) 411 (MH$^+$+Et$_3$N; 40), 332 (M+Na$^+$; 30), 310 (MH$^+$; 100), 101 (Et$_3$NH$^+$; 30).

EXAMPLE 55

Preparation of Ethyl 5-Methylnicitinoate

Commercially available 5-methylnicotinic acid (1.04 g; 7.6 mmol) was suspended in absolute ethanol (40 ml). Concentrated sulfuric acid (1 ml) was added, and the mixture was heated to reflux for 4 hours. The mixture was reduced in volume under reduced pressure at ambient temperature, diluted with ethyl acetate and washed with 1 N sodium hydroxide. The ethyl acetate was then washed with saturated sodium chloride solution, dried with anhydrous sodium sulfate and evaporated under reduced pressure at ambient temperature. This gave ethyl 5-methylnicitinoate (500.1 mg) as a colorless oil without further purification. $^1$H-NMR (CDCl$_3$) δ(ppm) 1.4 (t, 3H), 2.39 (s, 3H), 4.38 (q, 2H), 8.09 (s, 1H), 8.59 (s, 1H), 9.02 (s,1H).

EXAMPLE 56

Preparation of Ethyl 5-Methyl-3-piperidinecarboxylate

This reaction was run in the same manner as ethyl 3-piperidinylacetate, starting with ethyl 5-methylnicitinoate (491.5 mg; 2.98 mmol), L(+) tartaric acid (450 mg; 3.0 mmol), and platinum oxide (103.6 mg; 0.38 mmol), giving ethyl 5-methyl-3-piperidinecarboxylate (311.5 mg) as a light yellow oil. This material was used without further purification. MS m/z (positive ion) 172 (MH$^+$; 100).

EXAMPLE 57

Preparation of Ethyl 1-(2-Thiopheneacetyl)-5-methyl-3-piperidinecarboxylate

This reaction was run in the same manner as ethyl 1-benzoyl-3-piperidinecarboxylate, starting with ethyl 5-methyl-3-piperidinecarboxylate (311 mg; 1.82 mmol), diisopropylethylamine (350 µl; 2.01 mmol), and thiopheneacetyl chloride (225 µl; 1.83 mmol). Crude product was purified by distillation at approximately 220° C./0.1 torr, giving ethyl 1-(2-thiopheneacetyl)-5-methyl-3-piperidinecarboxylate (398 mg) as a yellow oil. MS m/z (positive ion) 467 (25), 296 (MH$^+$; 100).

EXAMPLE 58

Preparation of (S)±Ethyl 1-(2-Phenylpropionyl)-3-piperidinecarboxylate

This reaction was run in the same manner as ethyl 1-(3-thiophenecarbonyl)-3-piperidinecarboxylate, starting with commercially available 2-phenylpropionic acid (265 µl; 1.94 mmol), 1-(3-dimethylaminopropyl)-3-ethylcarbodiimide hydrochloride (371.3 mg; 1.94 mmol) and (S)-ethyl nipecotate (300 µl; 1.94 mmol). Crude product was purified by chromatography on silica eluting with 25% ethyl acetate/75% hexane, giving (S)±ethyl 1-(2-phenylpropionyl)-3-piperidinecarboxylate (268.9 mg) as a colorless oil. MS m/z (positive ion) 290 (MH$^+$; 100), 142 (55), 115 (50).

EXAMPLE 59

Preparation of (S)-Ethyl 1-(2-Thiopheneacetyl)-3-hydroxymethylpiperidine (S)-ethyl 1-(2-thiopheneacetyl)-3-piperidinecarboxylate (1.053 g; 3.75 mmol) was dissolved in absolute ethanol (40 ml). Sodium borohydride (2 g; 52.9 mmol) was added and this mixture was heated to reflux. The mixture was allowed to reflux for 1 hour and was then cooled to ambient temperature, diluted with dichloromethane and carefully quenched and washed with 1 N HCl. The dichloromethane was separated, washed with saturated sodium chloride solution, dried with anhydrous potassium carbonate, and evaporated under reduced pressure at ambient temperature. The crude product was purified by chromatography on silica eluting with 100% ethyl acetate, giving (S)-ethyl 1-(2-thiopheneacetyl)-3-hydroxymethylpiperidine (715.5 mg) as a thick colorless oil. MS m/z (positive ion) 501 (dimer+Na$^+$; 50), 488 (30), 262 (M+Na$^+$; 75), 249 (50), 240 (MH$^+$; 80), 102 (Et$_3$NH$^+$; 100).

EXAMPLE 60

Preparation of Ethyl 4-Methylnicitinoate

This reaction was run in the same manner as ethyl 5-methylnicitinoate, starting with commercially available 4-methylnicotinic acid hydrochloride salt (1.03 g; 5.95 mmol) in absolute ethanol, giving ethyl 4methylnicitinoate (756.8 mg) as light brown oil which was used without further purification. MS m/z (positive ion) 166 (M$^+$; 100), 138 (MH$^+$-OEt; 25).

EXAMPLE 61

Preparation of Ethyl 4-Methyl-3-piperidinecarboxylate

This reaction was run in the same manner as ethyl 3-piperidinylacetate, starting with ethyl 4-methylnicitinoate (750 mg; 4.55 mmol), L(+) tartaric acid (700 mg; 4.67 mmol), and platinum oxide (122.7 mg; 0.45 mmol), giving ethyl 4-methyl-3-piperidinecarboxylate (536.1 mg) as a light yellow oil. This material was used without further purification. MS m/z (positive ion) 172 (MH$^+$; 100).

EXAMPLE 62

Preparation of Ethyl 1-(2-Thiopheneacetyl)4-methyl-3-piperidinecarboxylate

This reaction was run in the same manner as ethyl 1-benzoyl-3-piperidinecarboxylate, starting with ethyl 4-methyl-3-piperidinecarboxylate (531.8 mg; 3.11 mmol), diisopropylethylamine (600 µl; 3.44 mmol), and thiopheneacetyl chloride (382 µl; 3.11 mmol). The crude product was purified by chromatography on silica eluting with 50% ethyl acetate/50% hexane, giving ethyl 1-(2-thiopheneacetyl)-4-methyl-3-piperidinecarboxylate (681.2 mg) as a yellow oil. MS m/z (positive ion) 397 (MH$^+$+Et$_3$N; 70), 296 (MH$^+$; 100).

EXAMPLE 63

Preparation of (S)-1-(2-Thiopheneacetyl)-3-piperidinecarboxaldehyde (S)-ethyl 1-(2-thiopheneacetyl)-3-hydroxymethylpiperidine (180.4 ml; 0.75 mmol) was dissolved in dichloromethane (20 ml). Crushed molecular sieves (0.25 g), and commercially available pyridinium dichromate (331.2 mg; 0.88 mmol) were added and the mixture was allowed to stir at ambient temperature for 5 hours. The mixture was then filtered through celite, washed with decolorizing carbon, filtered again and then evaporated under reduced pressure at ambient temperature. Crude product was purified by distillation at approximately 250° C./0.1 torr, giving (S)-1-(2-thiopheneacetyl)-3-piperidinecarboxaldehyde (58 mg) as a thick colorless oil. MS m/z (positive ion) 317 (25), 238 (MH$^+$; 100).

EXAMPLE 64

Preparation of (S)-1-(2-Thiopheneacetyl)-3-piperidinonitrile (S)-1-(2-thiopheneacetyl)-3-piperidinecarboxaldehyde (117.4 mg. 0.50 mmol) was dissolved in dichloromethane (2.5 ml). Anhydrous methanol (80 l), dry pyridine (100 g), and hydroxylamine hydrochloride (38.2 mg; 0.55 mmol) were added and the mixture was allowed to stir at ambient temperature for 1 hour. The mixture was then evaporated under reduced pressure at ambient temperature. The residue was suspended in fresh dichloromethane (3 ml). Dry pyridine (80 µl) was added to this mixture, followed by dropwise addition of commercially available phenylphosphonic dichloride (140 µl; 1.0 mmol). After addition was complete, the mixture was allowed to stir at ambient temperature for 22 hours. Saturated sodium bicarbonate solution was then added. The mixture was diluted with dichloromethane and washed with fresh saturated sodium bicarbonate solution. The dichloromethane was then washed with saturated sodium chloride solution, dried with anhydrous potassium carbonate, and evaporated under reduced pressure at ambient temperature. The crude product was purified by chromatography on silica eluting with 50% ethyl acetate/50% hexane, giving (S)-1-(2-thiopheneacetyl)-3-piperidinonitrile (71.4 mg) as a pale yellow oil. MS m/z (positive ion) 235 (MH$^+$; 100).

EXAMPLE 65

Preparation of (S)-Ethyl 1-Benzyl-3-piperidinecarboxylate (S)-ethyl nipecotate (309.1 mg; 1.97 mmol) was dissolved in anhydrous methanol (8 ml) and commercially available benzaldehyde (200 µl; 1.97 mmol) was added, followed by sodium cyanoborohydride (234 mg; 3.72 mmol). This mixture was allowed to stir at ambient temperature for 23 hours and was then diluted with dichloromethane. The dichloromethane was washed with water, then washed with saturated sodium chloride solution, dried with anhydrous potassium carbonate, and evaporated under reduced pressure at ambient temperature. The crude product was purified by chromatography on silica eluting with 50% ethyl acetate/50% hexane, giving (S)-ethyl 1-benzyl-3-piperidinecarboxylate (192.7 mg) as a colorless oil. MS mi/z (positive ion) 248 (MH$^+$; 100).

EXAMPLE 66

Preparation of (S)-N,N-Dimethyl-3-piperidinecarboxamide-L-(dibenzoyl)tartrate Salt To a solution of N,N-dimethyl-3-piperidinecarboxamide (4.32 g; 27.6 mmol;) in 43.2 ml of 2B-ethanol was added 4.95 g (13.8 mmol) di-benzoyl-L-tartaric acid. After heating to dissolve, the solvent was removed in vacuo leaving behind a white solid which was redissolved in 30.2 ml of 2B-ethanol with heating to reflux. Upon cooling to room temperature and stirring, the resultant white precipitate was collected via filtration and dried in vacuo to give (S)-N,N-dimethyl-3-piperidinecarboxamide-L-(dibenzoyl) tartrate salt in 38% yield (2.73 g) and 71% diastereomeric excess. This material was recrystallized from 27 ml of 99% 2B-ethanol by dissolving at reflux followed by cooling to room temperature and stirring for three hours. The white precipitate was collected by filtration and dried in vacuo to provide (S)-N,N-dimethyl-3-piperidinecarboxamide-L-(dibenzoyl) tartrate salt in 22% yield (1.55 g) and 99% diastereomeric excess.

EXAMPLE 67

Preparation of (S)-N,N-Dimethyl-3-piperidinecarboxamide (S)-N,N-dimethyl-3-piperidinecarboxamide-L-(dibenzoyl) tartrate salt (1.17 g; 2.28 mmol) was suspended in dichloromethane and shaken with 1N sodium hydroxide (6 ml). The dichloromethane was then dried with anhydrous potassium carbonate and evaporated under reduced pressure at ambient temperature, giving (S)-N,N-dimethyl-3-piperidinecarboxamide (275.3 mg) as a colorless oil, which was used without further purification. $^1$H-NMR (CDCl$_3$) δ (ppm) 1.5 (m, 1H), 1.7 (m, 2H), 1.85 (m, 1H), 2.65 (m, 2H), 2.85 (dd, 1H), 2.95 (s, 3H), 3.0 (m, 3H), 3.1 (s, 3H).

EXAMPLE 68

Preparation of (S)-Ethyl 1-Benzyl-3-piperidinecarboxylate 1-methiodide

This reaction was run in the same manner as ethyl 1-benzyl-3-piperidinecarboxylate 1-methiodide, starting with (S)-ethyl 1-benzyl-3-piperidinecarboxylate (156.4 mg; 0.63 mmol) and refluxing the mixture from the start. This gave (S)-ethyl 1-benzyl-3-piperidinecarboxylate 1-methiodide (78.4 mg) as an off white solid. MS m/z (positive ion) 262 (M$^+$; 100).

EXAMPLE 69

Preparation of N,N-Dimethyl-3-piperidinecarboxamide

This reaction was run in the same manner as ethyl 3-piperidinylacetate, starting with commercially available N,N-dimethylnicotinamide (10 g; 66.7 mmol) and platinum oxide (1.02 g; 4.49 mmol). Trifluoroacetic acid (5.1 ml; 66.2 mmol) was used in place of L(+) tartaric acid. Crude product was purified by distillation at approximately 150° C./10 torr, giving N,N-dimethyl-3-piperidinecarboxamide (4.0 g) as a colorless oil. MS m/z (positive ion) 157 (MH$^+$: 100).

EXAMPLE 70

Preparation of (S)-N,N-Dimethyl 1-benzyl-3-piperidinecarboxamide

This reaction was run in the same manner as ethyl 1-benzyl-3-piperidinecarboxylate, starting with (S)-N,N-dimethyl-3-piperidinecarboxamide (275 mg; 1.76 mmol), diisopropylethylamine (310 µl; 1.78 mmol), and benzyl bromide (210 µl; 1.77 mmol). Crude product was purified by chromatography on silica eluting with 5% methanol/95% dichloromethane, giving (S)-N,N-dimethyl 1-benzyl-3-piperidinecarboxamide (322.2 mg) as a colorless oil. MS m/z (positive ion) 247 (MH$^+$; 100).

EXAMPLE 71

Preparation of (S)-N,N-Dimethyl 1-Benzyl-3-piperidinecarboxamide 1-methiodide This reaction was run in the same manner as (S)-ethyl 1-benzyl-3-piperidinecarboxylate 1-methiodide, starting with (S)-N,N-dimethyl 1-benzyl-3-piperidinecarboxamide (295.2 mg; 1.2 mmol). This gave (S)-N,N-dimethyl 1-benzyl-3-piperidinecarboxamide 1-methiodide (390.4 mg) as a pale yellow solid. MS m/z (positive ion) 261 (M$^+$; 100).

EXAMPLE 72

Preparation of (S)-Ethyl 1-(2-Thiazyl)-3-piperidinecarboxylate

This reaction was run in the same manner as (S)-ethyl 1-benzyl-3-piperidinecarboxylate, starting with (S)-ethyl nipecotate (302.3 mg; 1.93 mmol) and commercially available 2-thiazolecarboxaldehyde (170 µl; 1.93 mmol). The crude product was purified by chromatography on silica eluting with 50% ethyl acetate/50% hexane, giving (S)-ethyl 1-(2-thiazyl)-3-piperidinecarboxylate (68.1 mg) was a pale yellow oil. MS m/z (positive ion) 255 (MH$^+$; 100).

EXAMPLE 73

Preparation of (S)-Ethyl 1-(2-Thiazyl)-3-piperidinecarboxylate 1-methiodide

This reaction was run in the same manner as (S)-ethyl 1-benzyl-3-piperidinecarboxylate 1-methiodide, starting with (S)-ethyl 1-(2-thiazyl)-3-piperidinecarboxylate (68 mg; 0.27 mmol). This gave (S)-ethyl 1-(2-thiazyl)-3-piperidinecarboxylate 1-methiodide (6.2 mg) as a yellow solid. MS m/z (positive ion) 269 (M$^+$; 100), 185 (100).

As stated above, some of the compounds of the present invention can be further reacted to form salts. The salts can be prepared using techniques well known in the art.

Reference will now be made to specific working examples of the methods of the present invention. The examples are provided to more completely describe preferred embodiments of the invention, and no limitation to the scope of the invention is intended thereby.

EXAMPLE 74

Various compounds of Formula I were evaluated for in vitro T-lymphocyte blastogenic activity with chicken leukocytes according to the steps described in the following procedure:

(a) Exsanguination step. The leukocytes were obtained from 3–6 week old Hubbard/Peterson broiler chickens. Initially, the chickens were rendered unconscious in a $CO_2$ chamber. The chickens were then exsanguinated via cardiac puncture. In the exsanguination procedure, a syringe was connected to a needle, and the needle was inserted into the area at the base of the neck under the "V" formed by the breast and sternum. After the needle was properly inserted, continuous vacuum was applied to a syringe (connected to the needle) by pulling back on the plunger. It is important to promptly carry out this withdrawal action, because there is only a 10–15 seconds time period after the blood has starting flowing into the syringe before the blood coagulates, and becomes unusable. As soon as the syringe is full (or prior to complete filling if too much time has elapsed such that the blood begins to coagulate), the whole uncoagulated blood is transferred to a tube having the anticoagulant EDTA therein. The tube is then rotated to mix the whole blood and the EDTA. Alternatively, the whole blood can be withdrawn directly into a vacuum container already having EDTA therein, rather than into a syringe.

(b) Leukocyte isolation step. Numerous methods for isolating leukocytes from (uncoagulated) whole blood are known in the art. In a preferred method, the sterile whole blood was combined with methylcellulose (1.5:1). Any blood containing clots was discarded. The mixture was centrifuged at 30×g for ten minutes (300 rpm on Beckman GS-6R centrifuge). The top layer (leukocytes in supernatant) was decanted into a sterile 50 ml conical tube, while taking care to prevent contamination of the sample by red blood cells. The decanted layer was then centrifuged at 200×g for ten minutes (1500 rpm on the Beckman GS-6R centrifuge). The supernatant liquid was discarded, and the resulting cell "pellet" was retained.

The cells were then washed in a solution containing 10 ml PBS (phosphate buffered saline) and Gentamycin (gentamicin sulfate) at a concentration of 50 $\mu$g/ml. This solution was centrifuged at 100×g (1000 rpm on the Beckman centrifuge) for five minutes, and the supernatant liquid was discarded. The washing step (including the centrifuging at 100×g) was repeated to ensure complete removal of the methylcellulose. The use of media such as DMEM (Dulbecco's Minimum Essential Medium) was avoided in the washing steps, since such media may cause agglutination of the white blood cells. Finally, the cells were then suspended in an appropriate media, such as RPMI 1640 tissue cell culture medium, supplemented with phenol red, $NaHCO_3$, and L-Glutamide. Supplemented RPMI 1640 is available from Sigma-Aldrich Chemical Co.

(c) Cell counting and cell viability step. The cells were counted and checked for viability using the Trypan Blue method of exclusion. 0.1 ml of the cell suspension was placed in a 4–5 ml small culture tube along with 0.7 ml HBSS (Hank's Buffered Saline Solution), available from Sigma-Aldrich, and 0.2 ml of a 0.4% solution of aqueous Trypan Blue stain, available from GIBCO BRL, of Grand Island, N.Y. The components were mixed thoroughly but gently, and allowed to sit for 5 minutes (no longer than 15 minutes). The components should not be exposed to the stain for extended periods of time, because such extended exposure may permit viable cells, as well as non-viable cells, to take up dye.

A cover slip was placed on a Bright Line hemacytometer, available from Howser Scientific, and 10 $\mu$l of the mixture from the tube was transferred to each chamber. Non-viable cells appear blue under a microscope. The viable cells in one of the 16-square corners of the hemacytometer were then counted. This cell count is verified by counting viable cells in a 16-square corner from the other side of the hemacytometer. The two counts are then averaged. If there appears to be a large percentage (greater than about 10%), of either non-viable cells or red blood cells in the sample, a differential leukocyte count is performed to compare the viable, non-viable and red blood cells. The total number of viable cells in each of the 16 squares is multiplied by 100,000 to obtain the total number of viable cells/ml.

(d) Differential leukocyte count. The differential (percentage) of leukocyte cell types was verified by making a 1:100 dilution of the $1 \times 10^7$ cell suspension media. 0.1–0.4 ml of suspended cells was placed in a cytospin funnel. The funnel was placed in a Shandon Cytospin, and balanced with an empty funnel assembly. The mixture was spun at 1000 rpm for 5 minutes. A slide was dipped (ten times) in each of the three solutions of a Hema 3 staining kit, namely, solutions of methanol, sodium azide, and a thiazine dye, respectively. The Hema 3 staining kit is available from Curtis-Matheson Scientific Co. The dipped end of each slide was blotted on a paper towel before dipping in a different solution.

The slides were then rinsed well (2 times each) in distilled water, and air dried. One drop of Permount mounting medium, available from Fisher Scientific, was placed on the slide, and a cover slip was placed over the medium. The medium was then allowed to dry. A differential count (200 cells) was performed, using either 40× or 100× (oil) objective. The percentage of each cell type (PMN's, lymphocytes and monocytes) was recorded. If the count showed a monocyte population of greater than about 20% of the total cell population, the cells were not used for the assay.

(e) Blastogenesis assay. Setup of the samples was performed in a Laminar flow hood, and aseptic techniques were utilized to prevent bacterial contamination. Compounds were filter sterilized after dilution. The immunopotentiator test compounds (prepared as described in the preceding examples) were weighed, and diluted in supplemented RPMI 1640 tissue cell culture medium. 0.2% Bovine Serum Albumin (BSA) was added to the tissue culture medium. The chicken leukocytes were diluted in supplemented RPMI 1640 to $6 \times 10^6$ cells/ml.

A 96-well sterile tissue culture plate (8 rows×12 columns) was provided, and a separate test was performed in each row. For each compound tested, 150 $\mu$l supplemented RPMI 1640 was added to the well in column 1. 125 $\mu$l supplemented RPMI 1640 was added to the wells in columns 2–12. 25 $\mu$l Concanavalin A (ConA, 20 $\mu$g/ml from frozen aliquots) was added to the well in column 2 as an internal standard (positive control). 25 $\mu$l samples of the test compound in various dilutions were added to the remaining wells in the row. Duplicate samples were tested at each dilution.

Each cell suspension was diluted 1:15 in the tissue cell culture medium, and placed in a cytospin funnel. The cells were spun, stained and counted as specified in the protocol described above, and the results of the differential were recorded. The samples were then incubated at 41° C. in a $CO_2$ incubator for 72 hours. The well plate was checked at 24 and 48 hours, and read at 72 hours. A test result is considered positive when a visual inspection (under magnification) reveals evidence of T-lymphocyte blastogenesis in the absence of other cell activation. If other cells are activated, the test result is considered negative, regardless of whether the lymphocyte is activated.

The results of these in vitro tests are provided in Table 1. The test results in the Table report the Minimum Stimulatory Concentration (MSC) of compound that was required to stimulate the T-lymphocytes to blastogenesis under the conditions of the present test, and the Maximum Tolerable Concentration (MTC) prior to causing cytotoxicity. If desired, cell death can be confirmed by performing assays for mitochondrial activity.

TABLE 1

| Compound of Example | MSC (units/ml) | MTC (units/ml) |
|---|---|---|
| 1 | 100 ng | 10 µg |
| 2 | 1 µg | 1 µg |
| 3 | 10 ng | 1 µg |
| 4 | 1 µg | 10 µg |
| 6 | 100 ng | 1 µg |
| 7 | 10 ng | 10 µg |
| 8 | 100 ng | 10 µg |
| 9 | 10 ng | 1 µg |
| 10 | 10 ng | 100 ng |
| 11 | 1 ng | 1 µg |
| 12 | 10 ng | 100 ng |
| 13 | 10 ng | 1 µg |
| 15 | 100 ng | 10 µg |
| 17 | 1 µg | 10 µg |
| 18 | 10 ng | 100 ng |
| 20 | 100 ng | 1 µg |
| 23 | 100 ng | 1 µg |
| 25 | 100 ng | 1 µg |
| 27 | 1 µg | 1 µg |
| 28 | 100 ng | 100 ng |
| 29 | 1 µg | 10 µg |
| 30 | 100 ng | 10 µg |
| 33 | 100 ng | 10 µg |
| 35 | 10 µg | 1 mg |
| 36 | 100 ng | 10 µg |
| 37 | 10 µg | 1 mg |
| 38 | 1 µg | 1 µg |
| 39 | 1 µg | 1 µg |
| 40 | 10 ng | 10 µg |
| 41 | 10 µg | 100 µg |
| 42 | 1 µg | 10 µg |
| 43 | 1 µg | 10 µg |
| 44 | 1 µg | 10 µg |
| 45 | 1 µg | 100 µg |
| 46 | 1 µg | 10 µg |
| 48 | 10 µg | 100 µg |
| 49 | 1 µg | 10 µg |
| 50 | 1 µg | 10 µg |
| 52 | 100 ng | 10 µg |
| 53 | 1 µg | 10 µg |
| 54 | 1 µg | 10 µg |
| 57 | 10 µg | 10 µg |
| 58 | 1 µg | 10 µg |
| 59 | 10 µg | 100 µg |
| 62 | 1 µg | 10 µg |
| 63 | 1 µg | 10 µg |
| 64 | 1 µg | 10 µg |
| 68 | 1 µg | 10 µg |
| 71 | 100 ng | 10 µg |
| 73 | 1 µg | 1 µg |

EXAMPLE 75

The compound prepared in Example 30, namely (S)-ethyl 1-(2-thiopheneacetyl)-3-peridinecarboxylate, was further evaluated for in vitro T-lymphocyte blastogenic activity from mammalian species other than avian.

The mammalian blastogenesis assays were conducted with the same protocol as the vian assays with the following exceptions:

1. Only mononuclear leukocytes are used for the mammalian assay. The cells are obtained from whole blood by differential centrifugation using Histopague 1.077 (Sigma Chemical Company, St. Louis, Mo).
2. 0.5% Fetal Bovine Serum (FBS) [GIBCOBRL, Grand Island N.Y.] is added to RPMI 1640 medium. Exception: Non-human primate plasma is used instead of FBS at 5 ml/liter to RPMI 1640 medium.
3. $5 \times 10^5$ cells/well were used with the mammalian assays.

The results of these in vitro tests are provided in Table 2:

TABLE 2

| SPECIES | MSC (units/ml) | MTC (units/ml) |
|---|---|---|
| Bovine | 10 µg | 1 mg |
| Canine | 1 µg | 100 µg |
| Non-human primate | 10 µg | 1 mg |
| Porcine | 10 µg | 1 mg |

Although many of the biologically active compounds described in Table 1 are racemic mixtures, in many cases it was determined that only the α, or (S), enantiomer accounted for the biological activity. Thus, for enhanced activity per unit, it is preferred to isolate and utilize the (S)-enantiomer.

The compounds of the present invention are immunopotentiator agents and the invention provides a method of stimulating the immune system of a host animal, including humans. The method comprises administering a compound preferably in the form of a pharmaceutical composition to a host animal needing or requiring immunostimulation, an effective amount of a compound, or composition, of the present invention.

The instant compounds can be administered orally or parenterally, individually or in combination, preferably parenterally, and usually in the form of a pharmaceutical composition. Parenteral routes of administration include intramuscular, intrathecal, intravenous, subcutaneous and intra-arterial. Doses, generally, will be from 2 µg/kg to 300 mg/kg per day, for 1–10 days, preferably from 1–5 days.

Compositions are prepared in a manner well known in the pharmaceutical art and comprise at least one active compound in association with a vehicle, diluent, excipient or carrier. Accordingly, the present invention includes pharmaceutical compositions comprising as active ingredient a compound of Formula I or II, associated with at least one pharmaceutically acceptable vehicle, carrier, diluent or excipient, and the invention further comprises the method of treating an animal requiring immunopotentiation using the compositions containing as an active ingredient a compound of Formula I or II.

In making the compositions of the present invention, as well as compositions containing other compounds of Formula I or II, the active ingredients are usually mixed with an excipient, diluted by an excipient, or enclosed within such a carrier which can be in the form of a capsule, sachet, paper or other container. When the excipierit serves as a diluent, it may be a solid, semi-solid or liquid material which acts as a vehicle, carrier or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Non-limiting examples of acceptable parenteral vehicles that may be mixed with the immunopotentiator compounds are a DMSO/peanut oil mixture, peanut oil alone, acetate buffered saline, phosphate buffered saline (PBS), isotonic saline or PEG 400.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum aracia, calcium silicate, microcrystalline cellulose, polyvinylpyrrolidone, cellulose, water, syrup and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the host animal by employing procedures well known in the art.

The compositions are preferably formulated in a unit dosage form with each dosage normally containing from 2 µg to 300 mg, more usually 2 µg to 200 mg of the active ingredient. The term "unit dosage form" refers to physically discrete units suitable as unitary dosages for human subjects and other animals, each unit containing a predetermined quantity of active material calculated to produce the desired therapeutic effect, in association with a suitable pharmaceutical excipient.

When administering the compound to a host animal, those skilled in the art will recognize that the optimal amount of the active compound to be administered in any particular instance will vary. Among the factors to be considered in determining a suitable dose are the identity of the host animal, the route of administration, whether single or multiple dosing is employed, the identity of the infectious agent, the present degree of immunocompetence of the host, the age of the host, and the specific compound to be administered. The specific amount to be administered to any particular species in any particular instance can be readily determined by those skilled in the art without undue experimentation when the above factors are considered.

As an example of the foregoing, for single dosing in chickens, a dose of from 50 µg/kg to 150 µg/kg has been found effective to reduce mortality and mean air sac lesions caused by *E. coli*. For multiple dosing in chickens, daily doses of 50 µg/kg over a 3-day period have been found effective. For single dosing in pigs, a 250 µg dose was found particularly effective in controlling *Actinobacillus pleuropneumoniae* (App).

The immunopotentiator compound must, of course, be delivered to the host in a satisfactory manner. Delivery mechanisms are well known in the art. A preferred method of delivery in animal species, such as farm animals, is parenteral administration, such as subcutaneous, intradermal, intramuscular, intraperitoneal or intravenous injection. In addition, the compounds may be administered via other well-known techniques, such as oral administration, in ovo administration, transdermal administration and spray inhalation. For oral administration, the compounds may be prepared in well-known forms such as tablets or capsules, as an aqueous liquid suspension, or, in the case of farm animals, as a feed supplement or drinking water medication. The compounds may also be administered to a maternal unit for delivery to a fetus. A suitable route for a particular application will normally depend on the identity and condition of the animal recipient.

The following examples illustrate the activity of immunopotentiator compounds administered to various species in vivo.

EXAMPLE 76

The compound prepared in Example 30, namely (S)-ethyl 1-(2-thiopheneacetyl)-3-piperidinecarboxylate, was utilized in a test formulation to investigate its efficacy to prevent or control the horizontal transmission of *Actinobacillus pleuropneumoniae* (App) 92C in a Seeder Pig Infection Model. The seeder pig model was chosen for the efficacy evaluation of the immunopotentiator compounds and analogs to prevent or control disease caused by App in recently weaned pigs. This model mimics a field outbreak of pneumonia in nursery pigs.

The animals tested were purchased from a commercial herd source known to be free of obvious disease and not recently on medication. There were a total of seventy-two (72) pigs, recently weaned and weighing in the approximate range of 15–20 pounds (6.8–9.1 kg). The challenged pigs were infected with an intranasal inoculation of *Actinobacillus pleuropneumoniae* (App), lyophilized #92C, a serotype 1, Iowa strain. The challenge material was a saline suspension containing a 2.5 hour log-phase growth broth culture, centrifuged and reconstituted at a concentration that contains $3 \times 10^7$ App 92C colony forming units (CFU) per pig in a 4 ml dose. An approved Animal Use Protocol governed the conduct of this trial.

Upon arrival, the pigs were double ear-tagged and divided into contact (48) and seeder (24) pig/groups. The seeder pigs were placed in two (2) groups of twelve (12) pigs per room (Groups 1). The contact pigs were placed in (8) groups of six (6) pigs per room (Groups 2–9). Lilly swine ration, AP11 SW and water were available ad libitum. All animals were observed daily and a room record was recorded.

Schedule of Events:

Day −5 Pigs arrive for the acclimation period of a minimum of 5 days.

Day 0 Daily individual observations of clinical impression signs begin and continue throughout the experiment. These were scored on a 0 to 3 scale (0=normal: alert, responsive; 1=slight: dyspnea, rough coat, slow to react; 2=moderate: lethargic, rough coat, breathing difficulty; 3=severe: unresponsive, breathing distress (open mouth).

Day 0 Individual animal weights of the contacts were taken.

Day 0 2 hours prior to infection of the seeder pigs, the contact pigs were injected via the intraperitoneal route with the test formulations. Two (2) rooms of six (6) pigs were treated with each of the following dose levels: 0 µg/pig, 125 µg/pig, 250 µg/pig, and 500 µg/pig.

Day 0 Twenty-four (24) seeder pigs were challenged with a dose containing 3×10 CFU of *Actinobacillus pleuropneumoniae* (App) 92C inoculum. The infected seeder pigs were then placed, 3 pigs per room, with the 6 treated contact pigs. To maximize the horizontal transmission of *App*, the living space in the rooms was reduced from 120 sq. ft. to 60 sq. ft., by placing partitions in the rooms.

Day +3 to +5 The seeder pigs were removed from all rooms. The pigs were euthanized, lung pathology was determined and lung cultures were taken. Moribund animals were euthanized. Any animals that succumbed to infection while on test were necropsied, lung lesions were scored and a sample was taken for bacterial isolation.

Day +14 The experiment was terminated. The contact pigs (Groups 2–9) were weighed, euthanized, and necropsied, with lung lesion scoring and bacterial culture assessment.

The test formulations were in an Acetate Buffered Saline vehicle. Samples were analyzed for potency. Data obtained was analyzed for weight gain, mortality, clinical impression scores, lung lesions, and bacteriologic recovery. Statistics were performed as appropriate to detect differences between groups.

Results:

| Treatment Groups | % Lung Lesions | % Lung Consolidation | App Reisolation | % Mortality |
| --- | --- | --- | --- | --- |
| 0 µg/pig | 73.5 | 18.6 | 65 | 27.2 |
| 125 µg/pig | 41.5 | 14.0 | 41.5 | 16.6 |
| 250 µg/pig | 0* | 0.44 | 0* | 0 |
| 500 µg/pig | 42.0 | 4.0 | 42 | 0 |

*indicates significant difference from controls at $P < 0.05$.

EXAMPLE 77

The compounds of Example 15 ((S)-ethyl 1-benzoyl-3-piperidinecarboxylate), Example 29 (1-benzoyl-3-butyrylpiperidine), Example 30 ((S)-ethyl 1-(2-thiopheneacetyl)-3-piperidinecarboxylate) and Example 68 ((S)-ethyl 1-benzyl-3-piperidinecarboxylate 1-methiodide), respectively, were tested to determine whether a single subcutaneous injection enhanced the bacterial clearance of *E. coli* from the peripheral blood of neonatal chicks. Bacterial clearance is a measurement of cell-mediated immunity, specifically, phagocyte function, in animals. An approved Animal Care and Use Committee protocol governed the activity in this experiment.

Materials:

1 ml syringes with 21 g 1" needles (Becton Dickinson and Company Franklin Lakes, N.J. 07417-1884); 1 ml syringe with 25 g ⅝" needles (Becton Dickinson and Company Franklin Lakes, N.J. 07417-1884); EMB agar plates (Difco Laboratories, Becton Dickinson Microbiology Systems, Sparks, Md. 21152); Culture tubes (14 ml polystyrene round bottom, Becton Dickinson Labware, Franklin Lakes, N.J. 07417-1886); Dulbecco's Phosphate Buffered Saline w/o $Mg^{++}$ or $Ca^{++}$ (Gibco BRL, Life Technologies Rockville, Md. 20850). Peterson x Hubbard male chicks (day of hatch from a commercial hatchery) were utilized 160 chicks were divided into 6 groups: Group 1=Controls (acetate-buffered saline vehicle); Group 2=Compound of Example 15 ((S)-ethyl 1-benzoyl-3-piperidinecarboxylate); Group 3=Compound of Example 29 (1-benzoyl-3-butyrylpiperidine); Group 4=Compound of Example 30 ((S)-ethyl 1-(2-thiopheneacetyl)-3-piperidinecarboxylate); Group 5=Compound of Example 68 ((S)-ethyl 1-benzyl-3-piperidinecarboxylate 1-methiodide); and Group 6=environmental controls. Groups 1–5 contained 3 replicates of 10 chicks each and Group 6 contained 1 replicate of 10 chicks.

Schedule of Events:

Day −2 Upon arrival, day of hatch chicks were randomized (10/group), and placed in a Petersime heated brooder battery unit (Petersime Incubator Company, Gettysburg, Ohio 45328). Chicks were injected subcutaneously in the caudal cervical region with 0.1 ml of 25 µg of test article (i.e., Vehicle or compound of Groups 2–5.) Previous experiments demonstrated that 25 µg was an optimal dose with these analogs using this method. All chicks were given ad libitum access to a commercially available starter feed and water.

Day 0 11:00 AM. Five to ten colonies of *E. coli* 19B were selected from a fresh overnight blood agar plate (TSA II with 5% sheep blood, Becton Dickinson Microbiology Systems Cockeysville, Md. 21030) and placed into 100 ml Brain Heart Infusion broth (Difco Laboratories, Becton Dickinson Microbiology Systems Sparks, Md. 21152) in a flask. The flask was incubated at 37° C. with shaking at 120 rpm for 4 hours.

3:00 PM Using a known standard curve, the bacterial stock solution was adjusted to $1 \times 10^8$ CFU of *E. coli*, and the bacterial stock solution was further diluted to $1 \times 10^6$ CFU/ml. The chicks in Groups 1–5 were injected in the left thigh muscle with 0.1 ml of the bacterial solution. The chicks in Group 6 were not challenged with bacteria.

Day 4 14–18 hours post-challenge, all chicks were euthanized (via $CO_2$) and then exsanguinated via cardiac puncture. EDTA tubes (Vacutainer EDTA 3 ml Draw tube, Becton Dickinson Vacutainer Systems, Franklin Lakes, N.J. 07417-1885) were used to collect 10 whole blood samples/group. Samples were kept on ice until they were processed. 0.1 ml whole blood was removed from a well-mixed sample tube, dropped onto the center on of a labeled EMB plate and spread evenly over the surface of the agar. EMB plates were placed in a 37° C. incubator overnight.

Day 5 EMB plates were removed from the incubator and bacterial colonies were counted and recorded to calculate CFU/ml/chick.

Data was transformed to logio values, and analysis of variance was used to determine significant differences between the treatment groups and controls. Data was expressed as the percentage of enhancedbacterial clearance compared to *E. coli*-challenged controls. Significance was reported at $P<0.05$.

Results:

| Treatment Groups | Test Article | E. coli Challenge | % Enhanced Clearance Compared to Controls |
| --- | --- | --- | --- |
| 1 | Vehicle | Yes | 0 |
| 2 | Ex. 15 compound | Yes | 34* |
| 3 | Ex. 29 compound | Yes | 33* |
| 4 | Ex. 30 compound | Yes | 61* |
| 5 | Ex. 68 compound | Yes | 50* |
| 6 | None | No | NA |

*indicates significant difference from controls at $P < 0.05$.

EXAMPLE 78

The compounds of Examples 11 and 30, namely ethyl 1-(N-methylaminocarbonyl)-4-oxo-3-piperidinecarboxylate and (S)-ethyl 1-(2-thiopheneacetyl)-3-piperidinecarboxylate, respectively, were tested to evaluate the efficacy of these compounds administered subcutaneously to growing chickens for the control of colibacillosis-associated mortality associated with E. coli. Two trials, Trial A and Trial B, respectively, were conducted according to an approved animal use protocol. The trials were conducted in a research facility utilizing used broiler litter as the source of bacteria to induce the infection. Eight (Trial A) or twenty-eight (Trial B) pens were required for this study. The pen represented the experimental unit. There were fifty chicks per pen. On the day-of-hatch, chicks were purchased as unvaccinated Peterson x Hubbard males from a commercial hatchery. The trials were conducted utilizing a randomized block design.

In Trial A there were two treatment levels of the compound of Example i 1:0 and 2 µg/chick with four pen replicates. In Trial B there were four treatment levels of the compounds of Example 30: 0, 2, 12.5 and 25 µg/chick with seven pen replicates. The chicks were randomly selected from the shipping containers, group weighed, administered either vehicle (phosphate-buffered saline) or compound (Example 11 or Example 30) and placed in pens with used litter. On day six (Trial A) or day thirteen (Trial B), the Newcastle's Disease Virus+Infectious Bronchitis Virus ($B_1$ Type, Lasota Strain) vaccine was administered through the drinking water. After vaccination, the stressor phase started with the removal feed and acute temperature changes. The studies were terminated on either day twenty-one (Trial A) or day twenty-nine (Trial B) of the live phase. Only chickens that are moribund or die while on study were necropsied and cultured for E. coli.

The trials were conducted in a multi-pen poultry house. The facility contained thirty-six pens all in the same air space, twenty-eight of which were selected for use. All pens had adequate and equivalent feeding and watering space. The number of chicks allotted to the available space within each pen (in square feet per chick) was dictated by standard commercial broiler production practices. The chicks used in the trials were unvaccinated Peterson x Hubbard male chicks from a commercial hatchery, and originating from a single breeder flock. The chicks were provided ad libitum access to specific commercial starter or grower rations manufactured at the Lilly Research Laboratories feed mill in Greenfield, Ind. All feeds were weighed and issued to individual pens. When the starter feed was changed to the grower feed, the feed was weighed back. The feed remaining at the end of the live phase was weighed back using the same weighback procedures and the data recorded.

Each pen within a location block was randomly assigned a treatment of either vehicle or compound (Example 11 or Example 30). Allotment of the chicks to trial pens occurred in the following manner. The chicks arrived at the trial facility on the day of hatch. The chicks were randomly selected, group weighed (50/pen) and assigned to trial pens. At the end of the trial, the chickens in each pen were group weighed by pen.

An infection model was utilized to induce colibacillosis in the broilers. The trials were conducted in research facilities utilizing used broiler litter with (Trial A) or without (Trial B) aerosol application of E. coli as the source of bacteria as well as the administration of Newcastle-Bronchitis Vaccine to induce the E. coli infection. The environmental stressors consisted of feed withdrawal for approximately 6–8 hour, removal of water for approximately 4–5 hour, and acute temperature changes which were based on clinical signs from the chickens and the administration of Newcastle-Bronchitis Vaccine. Only the acute temperature changes occurred throughout the stressor phase. The Newcastle-Bronchitis Vaccine (1 dose/chicken) was administered through the drinking water. The starting time of the daily stressor was determined by the ambient outside temperature. Clinical signs were used to determine proper temperature settings and the duration of the stressor period. The settings for the exhaust fans (controlled either manually or by computer) to remove the heat as soon as possible for an acute temperature change were determined by the outside ambient temperature.

E. coli associated mortality was verified by the following: airsacculitis, pericarditis, perihepatitis, peritonitis and a positive culture recovery of E. coli. All other causes of mortality were recorded as "other". Moribund chickens euthanized for humane purposes were treated as mortalities. All chickens dying or removed during the trial were individually weighed. These chickens were necropsied to determine the presumptive cause of death. Moribund chickens were adequately described, defined (e.g. recumbent/somnolent, unable to reach food and/or water, etc.). The date of each chickens death or removal was recorded.

Mortality caused by E. coli in a chicken was defined as death concurrent with at least one of the following: (1) a gross necropsy diagnosis of colibacillosis; or (2) a positive culture for E. coli. All chickens that died or were euthanized for humane purposes during the trial were necropsied and cultured for the presence of E. coli. Sterile swabs were used to collect E. coli bacteria for culture from the air sacs of each chicken at necropsy. Each swab was streaked on Eosin Methylene Blue (EMB) Agar plates and incubated for approximately 24 hours prior to reading the results. The results were categorical:

0=No growth of E. coli, or

1=Growth of E. coli.

The following variables were analyzed using either the chi square test of independence or analysis of variance:

Total Mortality

Colibacillosis-associated Mortality

Average Weight Gain/Chick

Feed to Gain

Results:

| Treatment Group | % Total Mortality | % Colibacillosis-associated Mortality | Average Weight Gain/Bird | Feed/Gain |
|---|---|---|---|---|
| Trial A: Example 11 compound | | | | |
| 0 µg | 26.0 | 25.0 | 1.38 lb (626 g) | 1.40 |
| 2 µg | 16.5* | 14.0 | 1.40 lb (635 g) | 1.35 |

*indicates significant difference from control within columns (P < 0.09)

| Treatment Group | % Total Mortality | % Colibacillosis-associated Mortality | Average Weight Gain/Bird (lbs) | Feed/Gain |
|---|---|---|---|---|
| Trial B: Example 30 compound | | | | |
| 0 µg | 20.3 | 8.3 | 2.53 lb (1.15 kg) | 1.56 |
| 2 µg | 93* | 5 | 2.53 lb (1.15 kg) | 1.56 |
| 12.5 µg | 10* | 2.8* | 2.44 lb (1.11 kg) | 1.59 |
| 25 µg | 14.3 | 6.8 | 2.49 lb (1.13 kg) | 1.57 |

*indicates significant difference from control within columns (P < 0.05)

Although it is envisioned that the immunopotentiators will, in most instances, be utilized as an alternative to the use of other agents, such as antibiotics, the invention also includes the use of immunopotentiators in combination with these agents. Such combined usage will, in most cases, allow the amount of the agents such as antibiotics that would otherwise be administered in the absence of the immunopotentiators to be reduced.

As demonstrated by the Examples provided herein, an effective amount of an immunopotentiator compound is useful for stimulating, or potentiating, the immune system of a host animal. It is known that, depending upon the particular dosage administered to the animal, an immunopotentiator agent may also have other effects on a host animal. The range of possible effects of an immunopotentiator on the immune system of the host animal include (1) no activity, (2) immune system stimulation, as demonstrated in the examples, and (3) immune suppression. Thus, under certain circumstances, an agent of this type may be useful as an immunosuppressant. Such use will find application in certain applications in which a suppressed immune function is desired, such as in allergy treatment and transplantation control.

We claim:

1. An immune system stimulating compound selected from ethyl 1-phenylacetyl-3-piperidinecarboxylate; ethyl 1-(4-fluorobenzoyl)-3-piperidinecarboxylate; ethyl (2-thiophenecarbonyl)-3-piperidinecarboxylate; ethyl 1-(2-thiopheneacetyl) -3-piperidinecarboxylate; ethyl 1-(N-methylaminocarbonyl)-4-oxo-3-piperidinecarboxylate; ethyl 1-(4-fluorobenzoyl)-4-oxo-3-piperidinecarboxylate; n-butyl 1-benzoyl-3-piperidinecarboxylate; N-ethyl 1-benzoyl-3-piperidinecarboxamide; N-(n-octyl) 1-benzoyl-3-piperidinecarboxamide; N-ethyl 1-(2-thiopheneacetyl-3-piperidinecarboxamide; ethyl 1-(3-(2-thienyl)propionyl)-3-piperidinecarboxylate; 2-dimethylaminoethyl 1-(2-thiopheneacetyl)-3-piperidinecarboxamide; 1-benzoyl-3-butyrylpiperidine; (S)-ethyl 1-(2-thiopheneacetyl)-3-piperidinecarboxylate; ethyl 1-(2-thiopheneacetyl-6-methyl-3-piperidinecarboxylate; ethyl 1-benzyl-3-piperidinecarboxylate 1-methiodide; ethyl 1-(4-phenylbenzoyl)-3-piperidinecarboxylate; (S)-1-(2-thiopheneacetyl)-3-piperidine carboxylic acid; 8-[(methylamino)carbonyl]-3-oxo-8-azabicyclo[3.2.1]octane-2-carboxylic acid, methyl ester; 1-(2-thiopheneacetyl-3-hydroxypiperidine; (S)-1-(2-thiopheneacetyl)-3-piperidinecarboxylic acid ammonium salt; ethyl 1-(1-phenylpropionyl)-3-piperidinecarboxylate; 1-(2-thiopheneacetyl)-3-(O-methanesulfonyl)piperidine; ethyl 1-(2-bromobenzoyl)-2-acetylpiperidinecarboxylate; 1-(2-thiopheneacetyl)-3-(O-propionyl)piperidine; (S)-ethyl 1-(N-benzylurea)-3-piperidinecarboxylate; (S)-ethyl 1-(N-methylurea)-3-piperidinecarboxylate; (S)-1-benzoyl-3-piperidinecarboxylic acid; (S)-methyl 1-benzoyl-3-piperidinecarboxylate; (S)-propyl 1-benzoyl-3-piperidinecarboxylate; (S)-ethyl 1-(2-thienylpropyl)-3-piperidinecarboxylate; ethyl 1-(2-thiopheneacetyl)-5-methyl-3-piperidinecarboxylate; (S)±ethyl 1-(2-phenylpropionyl)-3-piperidinecarboxylate; (S)-ethyl 1-(2-thiopheneacetyl)-3-hydroxymethylpiperidine; ethyl 1-(2-thiopheneacetyl)-4-methyl-3-piperidinecarboxylate; (S)-1-(2-thiopheneacetyl)-3-piperidinecarboxaldehyde; (S)-1-(2-thiopheneacetyl)-3-piperidinonitrile; (S)-ethyl 1-benzyl-3-piperidinecarboxylate 1-methiodide; (S)-N,N-dimethyl 1-benzyl-3-piperidinecarboxamide 1-methiodide or a physiologically acceptable salt of one of the foregoing.

2. An immune system stimulating compound of claim 1, which is ethyl 1-(2-thiopheneacetyl)-3-piperidinecarboxylate; ethyl 1-(N-methylaminocarbonyl)-4-oxo-3-piperidinecarboxylate; 1-benzoyl-3-butyrylpiperidine; (S)-ethyl 1-(2-thiopheneacetyl)-3-piperidinecarboxylate; (S)-1-(2-thiopheneacetyl)-3-piperidine carboxylic acid; or (S)-ethyl 1-benzyl-3-piperidinecarboxylate 1-methiodide; or a physiologically acceptable salt thereof.

3. A compound of claim 2, which is (S)-ethyl 1-(2-thiopheneacetyl)-3-piperidinecarboxylate or (S)-1-(2-thiopheneacetyl)-3-piperidine carboxylic acid or a physiologically acceptable salt thereof.

4. A compound of claim 3, which is (S)-ethyl 1-(2-thiopheneacetyl)-3-piperidinecarboxylate or a physiologically acceptable salt thereof.

5. A compound of claim 3, which is (S)-1-(2-thiopheneacetyl)-3-piperidinecarboxylic acid or a physiologically acceptable salt thereof.

6. An immunopotentiating composition comprising a physiologically acceptable carrier and an effective immune system stimulating amount of a compound selected from ethyl 1-phenylacetyl-3-piperidinecarboxylate; ethyl 1-(4-fluorobenzoyl)-3-piperidinecarboxylate; ethyl (2-thiophenecarbonyl)-3-piperidinecarboxylate; ethyl 1-(2-thiopheneacetyl)-3-piperidinecarboxylate; ethyl 1-(N-methylaminocarbonyl)-4-oxo-3-piperidinecarboxylate; ethyl 1-(4-fluorobenzoyl)-4-oxo-3-piperidinecarboxylate; n-butyl 1-benzoyl-3-piperidinecarboxylate; N-ethyl 1-benzoyl-3-piperidinecarboxamide; N-(n-octyl) 1-benzoyl-3-piperidinecarboxamide; N-ethyl 1-(2-thiopheneacetyl-3-piperidinecarboxamide; ethyl 1-(3-(2-thienyl)propionyl)-3-piperidinecarboxylate; 2-dimethylaminoethyl 1-(2-thiopheneacetyl)-3-piperidinecarboxamide; 1-benzoyl-3-butyrylpiperidine; (S)-ethyl 1-(2-thiopheneacetyl)-3-piperidinecarboxylate; ethyl 1-(2-thiopheneacetyl-6-methyl-3-piperidinecarboxylate; ethyl 1-benzyl-3-piperidinecarboxylate 1-methiodide; ethyl 1-(4-phenylbenzoyl)-3-piperidinecarboxylate; (S)-1-(2-thiopheneacetyl)-3-piperidine carboxylic acid; 8-[(methylamino)carbonyl]-3-oxo-8-azabicyclo[3.2.1]octane-2-carboxylic acid, methyl ester; 1-(2-thiopheneacetyl-3-hydroxypiperidine; (S)-1-(2-thiopheneacetyl)-3-piperidinecarboxylic acid ammonium salt; ethyl 1-(1-phenylpropionyl)-3-piperidinecarboxylate; 1-(2-thiopheneacetyl)-3-(O-methanesulfonyl)piperidine; ethyl 1-(2-bromobenzoyl)-2-acetylpiperidinecarboxylate; 1-(2-thiopheneacetyl)-3-(O-propionyl)piperidine; (S)-ethyl 1-(N-benzylurea)-3-piperidinecarboxylate; (S)-ethyl 1-(N-methylurea)-3-piperidinecarboxylate; (S)-1-benzoyl-3-piperidinecarboxylic acid; (S)-methyl 1-benzoyl-3-piperidinecarboxylate; (S)-propyl 1-benzoyl-3-piperidinecarboxylate; (S)-ethyl 1-(2-thienylpropyl)-3-piperidinecarboxylate; ethyl 1-(2-thiopheneacetyl)-5-methyl-3-piperidinecarboxylate; (S)±ethyl 1-(2-phenylpropionyl)-3-piperidinecarboxylate; (S)-ethyl 1-(2-thiopheneacetyl)-3-hydroxymethylpiperidine; ethyl 1-(2-thiopheneacetyl)-4-methyl-3-piperidinecarboxylate; (S)-1-(2-thiopheneacetyl)-3-piperidinecarboxaldehyde; (S)-1-(2-thiopheneacetyl)-3-piperidinonitrile; (S)-ethyl 1-benzyl-3-piperidinecarboxylate 1-methiodide; (S)-N,N-dimethyl 1-benzyl-3-piperidinecarboxamide 1-methiodide or a physiologically acceptable salt of one of the foregoing.

7. The composition of claim 6, wherein the compound is ethyl 1-(2-thiopheneacetyl)-3-piperidinecarboxylate; ethyl 1-(N-methylaminocarbonyl)-4-oxo-3-piperidinecarboxylate; 1-benzoyl-3-butyrylpiperidine; (S)ethyl 1-(2-thiopheneacetyl)-3-piperidinecarboxylate; (S)-1-(2-thiopheneacetyl)-3-piperidine carboxylic acid; or (S)-ethyl 1-benzyl-3-piperidinecarboxylate 1-methiodide; or a pharmaceutically acceptable salt of one of the foregoing.

8. The composition of claim 7, wherein the compound is (S)-ethyl 1-(2-thiopheneacetyl)-3-piperidinecarboxylate or (S)-1-(2-thiopheneacetyl)-3-piperidine carboxylic acid, or a physiologically acceptable salt thereof.

9. The composition of claim 8, wherein the compound is (S)-ethyl 1-(2-thiopheneacetyl)-3-piperidinecarboxylate or a physiologically acceptable salt thereof.

10. The composition of claim 8, wherein the compound is (S)-1-(2-thiopheneacetyl)-3-piperidinecarboxylic acid or a physiologically acceptable salt thereof.

11. A method for stimulating the immune system of a host animal, comprising administering to the host needing immunostimulation the composition of claim 6.

12. The method of claim 11, wherein the host animal is a member of the avian, bovine or porcine species.

13. The method of claim 11, wherein the host animal is a mammal.

14. A method for protecting a host animal against infection, comprising administering to a host animal in need of such protection the composition of claim 6.

15. The method of claim 14, wherein the method is for protecting the host animal against infection by *E. coli*.

16. The method of claim 15, wherein the host animal is a member of the avian species.

17. The method of claim 14, wherein the host animal is a member of the porcine species, and wherein the method is for protecting the host animal against infection by *Actinobacillus pleuropneumoniae*.

* * * * *